US010961284B2

(12) United States Patent
Cho et al.

(10) Patent No.: US 10,961,284 B2
(45) Date of Patent: Mar. 30, 2021

(54) **RECOMBINANT PROTEIN ANTIGEN OF *ORIENTIA TSUTSUGAMUSHI* AND VACCINE COMPOSITION USING THE SAME**

(71) Applicant: SEOUL NATIONAL UNIVERSITY R&DB FOUNDATION, Seoul (KR)

(72) Inventors: Nam Hyuk Cho, Seoul (KR); Na Young Ha, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 0 days.

(21) Appl. No.: 16/472,104

(22) PCT Filed: Dec. 21, 2017

(86) PCT No.: PCT/KR2017/015251
§ 371 (c)(1),
(2) Date: Jun. 20, 2019

(87) PCT Pub. No.: WO2018/117691
PCT Pub. Date: Jun. 28, 2018

(65) Prior Publication Data
US 2019/0330283 A1    Oct. 31, 2019

(30) Foreign Application Priority Data

Dec. 21, 2016  (KR) .................. 10-2016-0176031

(51) Int. Cl.
| | |
|---|---|
| *C07K 14/29* | (2006.01) |
| *A61K 39/02* | (2006.01) |
| *A61K 39/39* | (2006.01) |
| *C07K 16/12* | (2006.01) |
| *G01N 33/569* | (2006.01) |
| *A61K 39/00* | (2006.01) |

(52) U.S. Cl.
CPC .......... *C07K 14/29* (2013.01); *A61K 39/0233* (2013.01); *A61K 39/39* (2013.01); *C07K 16/1246* (2013.01); *G01N 33/56911* (2013.01); *A61K 2039/55505* (2013.01); *G01N 2469/10* (2013.01)

(58) Field of Classification Search
None
See application file for complete search history.

(56) References Cited

U.S. PATENT DOCUMENTS 7,335,477 B2 *  2/2008  Ching .................... C07K 14/29
435/7.1
2003/0165523 A1    9/2003  Ching et al.

FOREIGN PATENT DOCUMENTS

KR    2015-0123356 A    11/2015

OTHER PUBLICATIONS

International Search Report from corresponding PCT Application No. PCT/KR2017/015251, dated Apr. 24, 2018, with English translation.

* cited by examiner

*Primary Examiner* — Brian Gangle
(74) *Attorney, Agent, or Firm* — Harness, Dickey & Pierce, PLC

(57) ABSTRACT

The present invention discloses a novel recombinant protein antigen and a vaccine composition using the same, in which the novel recombinant protein antigen is derived from the conserved sequence of a TSA56 antigen and can be useful in the diagnosis of infection with *tsutsugamushi* and as a vaccine for *tsutsugamushi*.

19 Claims, 16 Drawing Sheets
Specification includes a Sequence Listing.

| | Amino acid sequences of identified conserved blocks |
|---|---|
| 17 genotypes | |
| Karp_C (SEQ ID NO. 1) | C1: SASAIELGDEGGLECGPYAKVGVVGGMITGVESTRLDPADADGKKHLSLTTGLPFGGTLAAGMTIAPGFRAELGVMYLTNI |
| | C2: KLTPPQPTIMPISIADRDFGID |
| | C3: RIAWLKNCAGIDY |
| | C4: WRHLVVGLAALSNANKPSASPVKVLSDKITQIYSDIK |
| | C5: LPNSASVEQIQNKMQELNDVLEELRDSFDGYISNAFANQIQLNF |
| | C6: QATAQEAVAAAAVRLLNGNDQIAQLYKDLVKLQRHAGIKKAMEKLAAQ |
| | C7: EAEFDLSMIVGQVKLYADVMTTESFS |
| Karp_B (SEQ ID NO. 2) | C1: SASAIELGDEGGLECGPYGKVGIVGGMITGVESTRLDSADAEGKKRLPLTTSMPFGGTLAAGMTIAQGFRAELGVMYLTNI |
| | C2: KLTPPQPTIMPISIADRDFGID |
| | C3: RIAWLKNYAGIDY |
| | C4: WRHLVVGLAALSNANKPSASPVKVLSDKITQIYSDVK |
| | C5: LPNSASVEQIQNKMQELNDLLEELRESFDGYLGGNAFANQIQLNF |
| | C6: QATAQEAVAAAAVRLLNGNDQIAQLYKDLVKLQRHAGIKKAMEKLAAQ |
| | C7: EAEFDLSMIVGQVKLYADLFITESFS |
| Karp_A (SEQ ID NO. 3) | C1: SASAIELGDEGGLECGPYAKVGVVGGMITGVESTRLDPADADGKKHLPLTTSMPFGGTLAAGMTIAQGFRAELGVMYLTNI |
| | C2: KLTPPQPTIMPISIADRDFGID |
| | C3: RIAWLKNCAGIDY |
| | C4: WRYLVVGLAALSNANKPSASPVKVLSDKITQIYSDIK |
| | C5: LPNSASVEQIQNKMQELNDVLEELRESFDGYLGGNAFANQIQLNF |
| | C6: QATAQEAVAAAAVRLLNGNDQIEQLYKDLVKLQRHAGIKKAMEKLAAQ |
| | C7: EAEFDLSMIVGQVKLYADVMITESFS |

Fig. 3

| | Amino acid sequences of identified conserved blocks |
|---|---|
| 17 genotypes | |
| Saitama (SEQ ID NO. 4) | C1: SASAIELGDEGGLECGPYAKVGVVGGMITGAESARLDQADTTGKKHLPLTTSMPFGGTLNAGITITPWLRAELGVMYLRNI |
| | C2: KLTPPQPTIMPISIADRDFAID |
| | C3: RVAWLKNYAGIDY |
| | C4: WRYMVIGLAALSNANKPSDPPVKVLSDKITQIYNDIR |
| | C5: LPNSASVEQIQNKMQELNELLEEVRDSFEGYIGGNAFANQIQLNF |
| | C6: QATAQEAAAAAAVRLLNGNDQIVQLYKDLVKLKRHAGFKKSMDKLAAQ |
| | C7: ETEFDLSMIVGQVKLYADLVATESFS |
| Boryong (SEQ ID NO. 5) | C1: SASAIELEDEVGLECGPYAKVGVVGGMITGAESTRLDSTDSEGKKHLSLTTGLPFGGTLAAGMTIAPGFRAELGVMYLRNI |
| | C2: KLTPPQPTMMPISIADRDFGID |
| | C3: RIAWLKNCAGIDY |
| | C4: WRSLVVGLAALSNANKPSASPVKVLSDKIIQIYSDIK |
| | C5: LPNSASIEQIQSKIQELGDTLEELRDSFDGYINNAFVNQIHLNF |
| | C6: QATAQEAVAAAAVRLLNGSDQIAQLYKDLVKLQRHAGIRKAMEKLAAQ |
| | C7: ETEFDLSMVVGQVKLYADLVTTESFS |
| JG_C (SEQ ID NO 6) | C1: SASAIELGDEGGLECGPYAKVGVVGGMITGVESTRLDPADADGKKHLPLTTSMPFGGTLAAGMTIAPGFRAELGVMYLRNI |
| | C2: KLTPPQPTIMPISIADRDEGVD |
| | C3: RIAWLKNYAGIDY |
| | C4: WRHLVVGVTALSHANKPSVTPVKVLSDKITKIYSDIR |
| | C5: LPNSASVEQIQAKMEELNNILEELRESFDGYLANAFANQIQLNF |
| | C6: QVTAQDAAAAAAVRALNGNEQIIQLYKDLVKLQRHAGIRKAMEQLAVQ |
| | C7: ETEFDLSMIVGQVKLYADLFTTESFS |

Fig. 4

| | Amino acid sequences of identified conserved blocks |
|---|---|
| 17 genotypes | |
| Kawasaki (SEQ ID NO. 7) | C1: SASAIELGDEGVLECGPYAKIGVVGGMVTGVESARLDPADVDCKKHLSLTTMLPFGGTLAAGMTIAPGFRAELGVMYLRNI <br> C2: KLTPPQPTIMPISIADRDLGVD <br> C3: RIAWLKNYAGIDY <br> C4: WRYLVVGVTALSNANKPSVSSVKVLSDKITQIYSDIR <br> C5: LPNSASVEQIQTKMQELNDVLEELRESFDGYLANAFANQIQLNF <br> C6: QVTAQEAAAAAAVRALNGNEQIIQLYKDLVKLQRHAGIRKAMEKLAAQ <br> C7: EVELDLSMIVAQVKLYADVVATESFS |
| JG_B (SEQ ID NO. 8) | C1: SASAMEFGDEGGGGLECGPYAKVGVVGGMITGVESTRLDSADAGGKRYLPLTTGLPFGGTLAAGMTIAPGFRAELGVMYLRNI <br> C2: KLVPPQPTIMPISIADRDVGVD <br> C3: RIAWLKNYAGIDY <br> C4: WRHLVVGVTALSHANKPSVTPVKVLSDKITKIYSDIR <br> C5: LPNSASVEQIQAKMQELNNVLEELRESFEGYLANAFANQIQLNF <br> C6: QVTAQEAAAAAAVRALNGNEQIIQLYKDLVKLQRHAGISKAMEQLAAQ <br> C7: ETEFDLSMVVGQVKLYADLVATESFS |
| JG_A (SEQ ID NO. 9) | C1: LASAIELGDEGGLECGPYAKVGVVGGMITGVESTRLDSADADGKKHLSLITGIPFGGTLAAGMTIAPGFRAELGVMYLRNI <br> C2: KLTPPQPTIMPISIADRDVGVD <br> C3: RIAWLKDYAGIDY <br> C4: WRHLVVGVTALSHANKPSVTPVKVLSDKITKIYSDIR <br> C5: LPNSASVEQIQAKMQELNNVLEELRESFDGYLANAFVNQIQLNF <br> C6: QVTAQEAAAAAAVRALNGNEQIIQLYKDLVKLQRHAGIRKAMEQLAAQ <br> C7: ETEFDLSMIVGQVKLYADLFTTESFS |

Fig. 5

|  | Amino acid sequences of identified conserved blocks |
|---|---|
| 17 genotypes | |
| Gilliam (SEQ ID NO. 10) | C1: SASAIELGEEGGLECGPYGKVGIVGGMITGAESTRLDSTDSEGKKHLSLTTGLPFGGTLAAGMTIAPGFRAELGVMYLRNI <br> C2: KLTPPQPTIMPISIADRDVGVD <br> C3: RIAWLKNYAGIDY <br> C4: WRHLVVGVTALSHANKPSVTPVKVLSDKITKIYSDIK <br> C5: LPNSASVEQIQSKMQELNDVLEDLRDSFDGYMGNAFANQIQLNF <br> C6: QATAQEAVAAAAVRLLNGNDQIAQLYKDLVKLQRHAGVKKAMEKLAAQ <br> C7: ETEFDLSMIVGQVKLYADLFTTESFS |
| TD (SEQ ID NO. 11) | C1: SASAIELGDEGGLECGPYAKVGVVGGIITGVESARLDPADTNGKKLLPLTTSMPFGGTLAAGMTIAQGFRAELGVMYLRNI <br> C2: KITPPQPTIMSISIADRNAGVD <br> C3: RIAWLRNYAGIEY <br> C4: WRHLVVGVAAMSNANKPSTSAVKVLGDKISQIYCDIK <br> C5: LPNSASVEQIQGKMQELGDLEALRDSFEGYIANAFANQIQLNF <br> C6: QVTAQEAVAAAAVRALNRNFQIAQLYKDLVKLQRHAGIRKAMEKLAAQ <br> C7: ETEFDLSMIVGQVKLYADLMTTESFS |
| TA763_B (SEQ ID NO. 12) | C1: SASAIELGDEGGLECGPYAKVGIVGGMITGAESTRLDSSDAEGKKRLSLTTSVPFGGTLAAGTIAQGFRAELGVMYLTNI <br> C2: KLTPPQPVIMPISTADRDMGVD <br> C3: RIAWLKQYAGIDY <br> C4: WRHLVVGIAALSNANKPSASPVKVLSDKITKIYSDIK <br> C5: LPNSASIEQIQRKMQELNDVLEGLRDAFDGYINNAFVDQIQLNF <br> C6: QATAQEAVAAAAVRLLNGNDQIVQLYKDLVKLQRHAGIKKAMEKLAAQ <br> C7: EAEFDLSMIVGQVKLYADLMTTESFS |

Fig. 6

| | Amino acid sequences of identified conserved blocks |
|---|---|
| 17 genotypes | |
| TA763_A (SEQ ID NO. 13) | C1: SASAIELGDEGGLECGPYAKVGVVGGMITGVESARLDPADHEGKKHLPLTTSMPFGGTLAAGMTIAQGFRAELGVMYLRNI |
| | C2: KLTPPQPTIMPISIADRDFGVD |
| | C3: RIAWLKEYAGIDY |
| | C4: WRHLVVGVTALSNANKPSASPVKILSEKITQIYSDIR |
| | C5: LPNSASVEQIQSKMQELSDLLEELRDSFDGYISNAFAGQIQLNF |
| | C6: QATAQEAVAAAAVRLLNGNDQIAQLYKDLVKLQRHAGIRKAMEKLAAQ |
| | C7: ETEFDLSMIVGQVKLYADLMTTESFS |
| Kato_B (SEQ ID NO. 14) | C1: SASAIELGDEGGLECGPYAKVGVVGGMITGVESTRLDPADAGGKKHLPLTTGLPFGGTLAAGMTIAPGFRAELGVMYLTNV |
| | C2: KLTPPQPTIMPISIADRDLGVD |
| | C3: RIAWLKNYAGIDY |
| | C4: WRHIVVGVTAMSNANKPSVSPVKVLSDKIVQIYRDVK |
| | C5: LPNSASVEQIQNKMQELNDILDDIRDSFDGCIGGNAFANQIQLNF |
| | C6: QATAQEAAAAAAVRVLNNNDQIIQLYKDLVKLKRHAGIKKAMEELAAQ |
| | C7: ETEFDLSMIVGQVKLYADLFTTESFS |
| Kato_A (SEQ ID NO. 15) | C1: SASAIELGEEGGLECGPYAKVGVVGGMITGVESTRLDPADVDGKKHLPLTTGLPFGGTLAAGMTIAPGFRAELGVMYLTNI |
| | C2: KLTPPQPTIMPISIADRDFGVD |
| | C3: RIAWLKEYAGIDY |
| | C4: WRDMVVGITAMSNANKPSASPIKVLSDKISQIYDDIR |
| | C5: LPNSASVEQIQSKMQELSETLEELRESFDGCIGNAFANQIQLDF |
| | C6: QATVQEATAAAAVRVLNGNGQIIQLYKDLVKLKRHAGIKKAMEKLAAQ |
| | C7: ETEFDLSMIVGQVKLYADLMTTESFS |

Fig. 7

|  | Amino acid sequences of identified conserved blocks |
|---|---|
| 17 genotypes | |
| Shimokoshi (SEQ ID NO. 16) | C1: SANAIEFDENSLECGPYAKVGIVGGVLSGVESARLDPADSEGKKHLPLIKGMPFGVTLAAGMTITPGVRAEISAMYLMNV<br>C2: KLTPPQPNIMPISIADRDIAVD<br>C3: RIAWLKNYAGIDY<br>C4: WRDVVVGITALSNANKPNVSAVKILSDKISQIYADIK<br>C5: LPDSASVDQIQNKVQELNKVLEDVRESFDGFILNAFAQPVRLNF<br>C6: AATAQEAAAAAAIRALNDGENNGIIQLYKDLYKLQRNVALKKSMKQLGDE<br>C7: EIEFDLHMAVGQVKLYADLFTIDSFS |
| TA686 (SEQ ID NO. 17) | C1: SASAIELGDEGGLECGPYARVGVVGGMITGVESTRLDSTDPEGKKHLSLTTGLPFGGTLAAGMTIAPGFRAELGVMYLRNI<br>C2: KLTPPPAIVMPISIADRDLGVD<br>C3: RIAWLKEYAGIDY<br>C4: WRHLVVGIAALSNANKPNASPVKVLSDKISQIYKDIK<br>C5: LANSASVEQIQSKMQELNDILEDLRESFDGYISNAFANQIQLDF<br>C6: HATAQEAAAAAAVRVLNNNEQIIQLYKDLVKLKRHAGIRKAMEQLAAQ<br>C7: ETEFDLSMIVGQVKLYADVFTTESFS |

Fig. 8

| | Amino acid sequences of identified conserved blocks |
|---|---|
| 5 genogroups | |
| Karp (SEQ ID NO. 18) | C1: SASAIELGDEGGLECGPYAKVGVVGGMITGVESTRLDSADADGKKHLPLTTSMPFGGTLAAGMTIAPGFRAELGVMYLTNI |
| | C2: KLTPPQPTIMPISIADRDFGID |
| | C3: RIAWLKNCAGIDY |
| | C4: WRHLVVGLAALSNANKPSASPVKVLSDKITQIYSDIK |
| | C5: LPNSASVEQIQNKMQELNDVLEELRDSFDGYIGGNAFANQIQLNF |
| | C6: QATAQEAVAAAAVRLLNGNDQIAQLYKDLVKLQRHAGIKKAMEKLAAQ |
| | C7: EAEFDLSMIVGQVKLYADLVITESFS |
| Gilliam (SEQ ID NO. 19) | C1: SASAIELGDEGGLECGPYAKVGVVGGMITGVESTRLDSADADGKKHLSLTTGLPFGGTLAAGMTIAPGFRAELGVMYLRNI |
| | C2: KLTPPQPTIMPISIADRDVGVD |
| | C3: RIAWLKNYAGIDY |
| | C4: WRHLVVGVTALSHANKPSVTPVKVLSDKITKIYSDIR |
| | C5: LPNSASVEQIQAKMQELNDVLEELRESFDGYLANAFANQIQLNF |
| | C6: QVTAQEAAAAAAVRALNGNEQIIQLYKDLVKLQRHAGIRKAMEQLAAQ |
| | C7: ETEFDLSMIVGQVKLYADLFTTESFS |
| TA763 (SEQ ID NO. 20) | C1: SASAIELGDEGGLECGPYAKVGVVGGMITGVESTRLDSADAEGKKHLPLTTSMPFGGTLAAGMTIAQGFRAELGVMYLTNI |
| | C2: KLTPPQPVIMPISTADRDMGVD |
| | C3: RIAWLKQYAGIDY |
| | C4: WRHLVVGIAALSNANKPSASPVKVLSDKITQIYSDIK |
| | C5: LPNSASVEQIQSKMQELSDLLEELRDSFDGYISNAFAGQIQLNF |
| | C6: QATAQEAVAAAAVRLLNGNDQIAQLYKDLVKLQRHAGIRKAMEKLAAQ |
| | C7: ETEFDLSMIVGQVKLYADLMTTESFS |

Fig. 9

| | Amino acid sequences of identified conserved blocks |
|---|---|
| 5 genogroups | |
| Kato (SEQ ID NO. 21) | C1: SASAIELGDEGGLECGPYAKVGVVGGMITGVESTRLDPADVDGKKHLSLTTGLPFGGTLAAGMTIAPGFRAELGVMYLTNV<br>C2: KLTPPQPTIMPISIADRDFGVD<br>C3: RIAWLKEYAGIDY<br>C4: WRHLVVGVTAMSNANKPSVSPVKVLSDKIVQIYRDIK<br>C5: LPNSASVEQIQNKMQELNDILEEIRDSFDGCIGGNAFANQIQLNF<br>C6: QATAQEAAAAAAVRVLNNNDQIIQLYKDLVKLKRHAGIKKAMEKLAAQ<br>C7: ETEFDLSMIVGQVKLYADLFTTESFS |
| Shimokoshi (SEQ ID NO. 22) | C1: SANAIELDENSLECGPYAKVGIVGGVLSGVESARLDPADSEGKKHLPLIKGMPFGVTLAAGMTITPGVRAEISAMYLMNV<br>C2: KLTPPQPNIMPISIADRDIGVD<br>C3: RIAWLKNYAGIDY<br>C4: WRDVVVGITALSNANKPNVSAVKVLSDKISQIYADIK<br>C5: LPDSASVEQIQNKVQELNKVLEDVRESFDGFILNAFAQQVQLNF<br>C6: AATAQEAAAAAAVRALNDGENNGIIQLYKDLYKLQRHVALKKSMEQLGAE<br>C7: EIEFDLHMAVGQVKLYADLFTIDSFS |

Fig. 10

| | Amino acid sequences of identified conserved blocks |
|---|---|
| Universal conserved blocks | |
| (SEQ ID NO. 23) | C1: SASAIELGDEGGLECGPYAKVGVVGGMITGVESTRLDSADADGKKHLPLTTGMPFGGTLAAGMTTAPGFRAELGVMYLTNI<br>C2: KLTPPQPTIMPISIADRDFGVD<br>C3: RIAWLKNYAGIDY<br>C4: WRHLVVGVTALSNANKPSVSPVKVLSDKITQIYSDIK<br>C5: LPNSASVEQIQNKMQELNDVLEELRDSFDGYIGNAFANQIQLNF<br>C6: QATAQEAAAAAAVRALNGNDQIIQLYKDLVKLQRHAGIKKAMEKLAAQ<br>C7: ETEFDLSMIVGQVKLYADLFTTESFS |

Fig. 11

```
SASAIELEDE VGLECGPYAK VGVVGGMITG AESTRLDSTD SEGKKHPGFR  50
AELGVMYLRN IKLTPPQPTM MPISIADRDF GIDRIAWLKN CAGIDYWRSL 100
VVGLAALSNA NKPSASPVKV LSDKIIQIYS DIKLPNSASI EQIQSKIQEL 150
GDTLEELRDS FDGYINNAFV NQIHLNFQAT AQEAVAAAAV RLLNGSDQIA 200
QLYKDLVKLQ RHAGIRKAME KLAAQETEFD LSMVVGQVKL YADLVTTESFS 251
```

RECOMBINANT PROTEIN ANTIGEN OF ORIENTIA TSUTSUGAMUSHI AND VACCINE COMPOSITION USING THE SAME

CROSS-REFERENCE TO RELATED APPLICATIONS

This application is a national phase application of PCT Application No. PCT/KR2017/015251, filed on 21 Dec. 2017, which claims benefit of Korean Patent Application 10-2016-0176031, filed on 21 Dec. 2016. The entire disclosure of the applications identified in this paragraph are incorporated herein by reference. The present invention relates to a novel recombinant protein antigen of *Orientia tsutsugamushi* and a vaccine composition using the same.

FIELD

The present invention relates to a novel recombinant protein antigen of *Orientia tsutsugamushi* and a vaccine composition using the same.

BACKGROUND

*Tsutsugamushi* disease (scrub typhus) is an arthropod-mediated infectious disease occurring when chigger mite larvae infected with *Orientia tsutsugamushi* (hereinafter referred to as "*tsutsugamushi*") bite a person, and it is estimated that at least one million patients are afflicted annually, mainly in the Asia-Pacific region, such as the Russian Federation, Korea, Japan, China, Southeast Asia, northern Australia and the like. Patients who are bitten by infected chigger mite larvae show symptoms such as fevers, chills, scab formation, rash, myalgia and lymphadenopathy through an incubation period of 1 to 2 weeks. If the disease is diagnosed at an early stage of infection, treatment with appropriate antibiotic prescription is possible, but early clinical symptoms are similar to other febrile infectious diseases, and thus distinguishing the same at the time of diagnosis is difficult, and moreover, there is no convenient and quick diagnostic method in the clinical field. Hence, development to severe systemic febrile illness is frequent, and the number of deaths every year is high.

*Tsutsugamushi* is known to have a wide variety of serotypes or genotypes, and is classified into tens of subtypes (strains), including prototypes such as Gilliam, Karp and Kato, which are traditionally known (Eisemann and Osterman 1985, Am. J. Trop. Med. Hyg. November; 34(6):1173-8; Akira Tamura and Akiyoshi Kawamura 1991, J. Clin. Microbiol. February 1991, Vol. 29, No. 2; WOO-HYUN CHANG et al. 1993, J. Clin. Microbiol. March 1993, p. 598-605). The genotypes of *Tsutsugamushi* are classified based on a gene encoding a 56 kDa type-specific antigen (TSA56), which is the main membrane protein of this bacterium. In Korea, most infections are of the Boryong genotype, which is similar to the Karp genotype, and the kinds and frequencies of genotypes of *tsutsugamushi*, which are found in countries where *tsutsugamushi* disease is occurring, are known to vary widely.

Protective immunity induced by infection with *tsutsugamushi* in a human or mouse infection model is known to be specific to the genotype of infected *tsutsugamushi*, and the persistence of the antibody response is relatively short, on the order of 1 to 2 years. No protective immunity is conferred upon secondary infection with an additional genotype. For example, a case of *tsutsugamushi* disease has been reported in a patient who was infected with Gilliam serotype and was then re-infected with Karp serotype after 2 months. Because of the genetic diversity of *tsutsugamushi*, effective vaccines have not yet been developed, and serologic diagnosis of this disease is difficult. In recent years, there have been reports of antibiotic resistant bacteria in Southeast Asia, India and the like, and increasing numbers of cases are reported in East Asia, including Korea and China, which is a major public health problem. Accordingly, there is a growing need to develop techniques that are able to effectively and rapidly diagnose infection with a variety of *tsutsugamushi* genotypes and to provide effective protective immunity.

Various studies have been conducted over the past 70 years with the goal of developing *tsutsugamushi* vaccines. In the early development of the *tsutsugamushi* vaccine, a killed vaccine resulting from formalin treatment or gamma irradiation was found to be unable to provide effective protective immunity to humans, and recombinant protein vaccines (Subunit vaccine) using TSA56 (56-kDa Type-Specific Antigen) protein and 47 KDa outer membrane protein, DNA vaccines and the like have been studied, but these vaccines have been reported to induce transient protective immunity only for infection with the same genotype, and have not been shown to induce protective immunity against other genotypes (Buckland and Dudgeon, 1945; Lancet 2, 734-737; Kawamura et al., 1940. Trop. Dis. Bull. 37, 269-270; Seong et al., 1997. Infect. Immun. 65, 1541-1545; Yu et al., 2005. Am. J. Trop. Med. Hyg. 72, 458-46).

Therefore, it is necessary to overcome these genetic differences and develop vaccine antigens capable of providing universal protective immunity against various genotypes or serotypes. It is also urgently required to develop diagnostic antigens that are needed to diagnose various genotypes effectively and early.

SUMMARY

Technical Problem

Accordingly, an objective of the present invention is to provide a novel recombinant protein antigen of *Orientia tsutsugamushi*.

Another objective of the present invention is to provide a vaccine composition for *Orientia tsutsugamushi* using the recombinant protein antigen.

Still another objective of the present invention is to provide a diagnostic composition for *Orientia tsutsugamushi* using the recombinant protein antigen.

Other or particular objectives of the present invention will be described below.

Technical Solution

As confirmed in Examples, which will be described later, the present inventors collected 1,030 TSA56 protein gene sequences published before Dec. 31, 2015 from the base sequence database of the National Center for Biotechnology Information, among which 206 genes including 85% or more of the coding site (ORF site) of the entire TSA56 protein sequence were selected (in the tsa56 gene sequences listed in the National Center for Biotechnology Information, sequences containing the entire ORF and only a part thereof are present, and thus, among these gene sequences, genes including a site encoding an amino acid sequence corresponding 85% or more to the entire TSA protein amino acid sequence of the corresponding strain are selected), and the amino acid sequences and base sequences of these 206 genes were analyzed and classified into 17 genotypes showing statistically significant differences therebetween, which were then further classified into 5 genogroups based on the distances therebetween in a phylogenetic tree. For these genotypes, conserved blocks having relatively small genotypic variation were defined as seven sections (C1 to C7) having high consistency and low nonspecific changes of consecutive amino acid sequences using a Gblocks program (Systematic biology, 2007, 56, 564-577), and the amino acid sequences of the genes included in the 17 genotypes were compared with each other to define the amino acid at each position having the highest frequency among the amino acid sequences included in the seven conserved blocks, and a sequence (representative sequence) representing the entire sequence was derived based thereon.

Then, the present inventors produced a recombinant protein antigen in which seven conserved block sequences of Boryong genotype as a typical example, among the 17 genotype sequences, 5 genogroup sequences and 1 representative sequence, are connected (the amino acid sequence of "LSLTTGLPFGGTLAAGMTIA" (SEQ ID NO: 25) was removed from the C1 conserved block because this amino acid sequence was predicted to constitute the transmembrane motif and was confirmed to inhibit the production of the recombinant protein) through expression/purification in *Escherichia coli*, and ascertained that, in order to evaluate the likelihood of use of the recombinant protein for diagnosis, the recombinant protein was determined to have reactivity similar to a Boryong TSA56 antigen based on the results of measurement of reactivity through western blotting and ELISA after reaction with *tsutsugamushi*-infected antiserum, and moreover, in order to evaluate the likelihood of use of the recombinant protein as a vaccine, when mice were immunized with the recombinant protein antigen, humoral immunity such as antibody production to TSA56 was effectively induced, and the mice immunized with the recombinant protein antigen also exhibited high resistance to other genotypes compared to the test group immunized with the TSA56 antigen.

An aspect of the present invention pertains to a recombinant antigen protein comprising any one sequence of SEQ ID NOS: 1 to 23 in which seven conserved block sequences of C1 to C7 are connected in order in each of 17 genotypes of FIGS. 3 to 8, 5 genogroups of FIGS. 9 and 10, and 1 representative sequence of FIG. 11. Moreover, when a recombinant protein antigen was prepared using the representative sequence and mice were immunized therewith, the survival rate of *tsutsugamushi*-infected mice was confirmed to be higher than that of a comparative group (TSA56 antigen-immunized mice).

Preferably, the recombinant antigen protein is configured such that the amino acid sequence of the section predicted as the transmembrane helix (in the Boryong genotype, LSLTTGLPFGGTLAAGMTIA (SEQ ID NO: 25) from the 47$^{th}$ amino acid to the 66$^{th}$ amino acid) is removed from each C1. The section of the transmembrane helix may be searched for in the C1 sequence of each of 17 genotypes of FIGS. 3 to 8, 5 genogroups of FIGS. 9 and 10, and 1 representative sequence of FIG. 11, by finding the sequence corresponding to the Boryong genotype sequence or using a TMHMM Server v. 2.0 program (http://www.enzim.hu/hmmtop/) that enables the prediction of such a section.

As described above, among the recombinant protein antigens comprising 23 amino acid sequences, the recombinant protein antigen for Boryong strain as a typical example manifests reactivity similar to the TSA56 antigen for the *tsutsugamushi*-infected antiserum, thus showing not only a diagnosis effect but also an effect as a vaccine by inducing an immune response against other genotypes compared to the TSA56 antigen. It is known that TSA56 or a conventional recombinant protein vaccine using the same does not induce an immune response against other genotypes (Seong et al., 1997. Infect. Immun. 65, 1541-1545; Yu et al., 2005. Am. J. Trop. Med. Hyg. 72, 458-46).

Meanwhile, each sequence has a sequence homology of at least 68.8% with the representative sequence, and it is understood that recombinant antigens that include a sequence common to the representative sequence and have a sequence homology of 68.8% or more therewith also fall within the scope of the present invention. As used herein, "a sequence common to a representative sequence" refers to a sequence comprising common amino acids in all of 23 sequences at individual positions when the representative sequence and the remaining 22 sequences are aligned.

Another aspect of the present invention pertains to a gene encoding the recombinant protein antigen, and still another aspect of the present invention pertains to a method of preparing a recombinant protein antigen using the gene.

The preparation method according to the present invention may be performed through recombinant DNA technology known in the art using the gene encoding the recombinant protein antigen. This method includes (i) preparing an expression vector including a gene encoding the recombinant protein antigen, (ii) transforming the expression vector into host cells, (iii) culturing the transformed host cells, and (iv) isolating and purifying the recombinant protein antigen from the resultant culture broth.

A target gene encoding a target protein (a protein to be produced), which is the recombinant protein antigen, may be chemically synthesized based on the target protein sequence encoded by the gene. Such chemical synthesis methods are well known in the art, and, for example, solid-phase synthesis technology, solution-phase synthesis technology and the like may be used, and commercially available automated DNA synthesizers and the like using these technologies may be used. Regarding details thereof, reference may be made to the document [Nucl. Acid Res. 14:5399-5467, 1986], the document [Tet. Lett. 27:5575-5578, 1986], the document [Nucl. Acid Res. 4:2557, 1977], the document [Lett., 28:2449, 1978] and the like.

In the present invention, the expression vector may be a nucleic acid in the form of a plasmid, a cosmid, a phagemid, a phage or the like. Depending on the host microorganism, an appropriate vector may be purchased among commercially available vectors, or may be used after being purchased and modified. For example, when *Escherichia coli* is used as the host microorganism, pUC19, pSTV28, pBBR1MCS, pBluscriptII, pBAD, pTrc99A, pET, pACYC184, pBR322, pJE101, pJE102, pJE103, etc. may be used.

There is a considerable quantity of literature in the art about the expression vector construction including recombinant DNA technology, and for example, reference may be made to the document [Sambrook et al., Molecular Cloning, A Laboratory Manual, Cold Spring Harbor Laboratory Press, (2001)], the document [F M Ausubel et al, Current Protocols in Molecular Biology, John Wiley amp; Sons, Inc. (1994)], the document [Marston, F (1987) DNA Cloning Techniques] and the like. All of the documents cited in the present specification are considered part of the present specification, unless otherwise stated.

The expression vector includes a regulatory sequence that affects transcription and translation of the target gene by being operably linked to the target gene, in addition to the target gene encoding the recombinant protein antigen.

Such a regulatory sequence usually includes a promoter sequence, a transcription termination signal sequence (polyadenylation signal), and the like. As used herein, the term "being operably linked" means a linkage such that the transcription and/or translation of a gene are affected. For example, if a promoter affects the transcription of a gene linked thereto, the promoter and the gene are regarded as operably linked.

As used herein, the term "promoter" follows the typical meaning known in the art, and particularly refers to a nucleic acid sequence having a function of controlling transcription of one or more genes, which is located upstream (5' side) of the transcription initiation point of a gene and includes a binding site for a DNA-dependent RNA polymerase, a transcription initiation point, a transcription factor binding site, and the like. When derived from a prokaryotic organism, the promoter includes a Pribnow box (at a position near −10 with respect to the transcription initiation point (+1)) or a Hogness box (at a position near −35 with respect to the transcription initiation point (+1)) upstream of the transcription initiation point, and when derived from a eukaryotic organism, the promoter includes a TATA box (at position −20 to −30 with respect to the transcription initiation point (+1)) upstream of the transcription initiation point, a CAAT box (at a position near −75 with respect to the transcription initiation site), an enhancer, a transcriptional repressor, etc.

So long as the promoter is capable of expressing the target gene linked thereto, any of a constitutive promoter (a promoter that induces expression constantly in a certain organism) and an inducible promoter (a promoter that induces expression of a target gene in response to a certain external stimulus) may be used. Preferably, a promoter suitable for a certain host microorganism is used. For example, when *Escherichia coli* is used as the host microorganism, a promoter such as T7A1, T7A2, T7A3, λpL, λpR, lac, lacUV5, trp, tac, trc, phoA, rrnB, or 1PL may be used, and when yeast is used as the host microorganism, a promoter such as GAL1, GAL10, ADH1, TDH3, or PGK may be used.

The expression vector is configured to include a terminator sequence which is a transcription termination sequence, in addition to the promoter. The terminator sequence is a sequence that acts as a poly(A) addition signal (polyadenylation signal) to increase the completeness and efficiency of transcription. Suitable terminator sequences, depending on the host microorganism, are known in the art, and, for example, when the host microorganism is *Escherichia coli*, a tac terminator sequence, an rrnB terminator sequence and the like may be used, and when the host microorganism is yeast, an ADH1 terminator sequence and the like may be used.

The expression vector may further include a selectable marker gene. The selectable marker gene is a gene encoding a trait that enables selection of a host microorganism containing such a marker gene, and is generally an antibiotic resistance gene. Examples of such a useful antibiotic resistance gene may include a puromycin resistance gene (for example, a puromycin N-acetyltransferase gene derived from *Streptomyces alboniger*), a neomycin resistance gene (for example, an aminoglycoside phosphotransferase gene derived from *Streptomyces fradiae*), a hygromycin resistance gene (for example, a hygromycin phosphotransferase gene derived from *Streptomyces hygroscopicus*), a bleomycin resistance gene (for example, a bleomycin binding protein derived from *Streptomyces verticillus*), a blasticidin resistance gene (for example, a blasticidin S-acetyltransferase gene derived from *Streptomyces verticillum*), a hygromycin resistance gene (for example, an aminocyclitol phosphotransferase gene derived from *Escherichia coli*), an ampicillin resistance gene (β-lactamase gene), and the like.

In the method of the present invention, the expression vector may also include a restriction enzyme recognition site for easy cloning of the target gene.

In the method of the present invention, the expression vector prepared in step (a) may be transformed into the host microorganism in step (b).

Transformation refers to the modification of a genotype of a host microorganism due to the introduction of a target gene, and the introduced foreign gene may be present independently of the genome of the host microorganism or in the state of being incorporated into the genome of the host organism.

Methods of transforming the expression vector into the host microorganism are also known in the art, and any of the known methods may be selected and used. For example, when the host microorganism is prokaryotic cells such as *Escherichia coli*, the transformation may be carried out through a $CaCl_2$ method, a Hanahan method, an electroporation method, a calcium phosphate precipitation method, or the like, and when the host microorganism is eukaryotic cells such as yeast, a microinjection method, a calcium phosphate precipitation method, an electroporation method, a liposome-mediated transfection method, a DEAE-dextran treatment method, a gene bombardment method, or the like may be used. Regarding details of the transformation method, reference may be made to the document (Cohen, S. N. et al., Proc. Natl. Acad. Sci. USA, 9:2110-2114(1973)), the document (Hanahan, D., J. Mol. Biol., 166:557-580 (1983)), the document (Dower, W. J. et al., Nucleic. Acids Res., 16:6127-6145(1988)) (Capecchi, M. R., Cell, 22:479 (1980)), the document (Graham, F. L. et al., Virology, 52:456(1973)), the document (Neumann, E. et al., EMBO J., 1:841(1982)), the document (Wong, T. K. et al., Gene, 10:87(1980)), the document (Gopal, Mol. Cell Biol., 5:1188-1190(1985)), the document (Yang et al., Proc. Natl. Acad. Sci., 87:9568-9572(1990)), the document (Maniatis et al., Molecular Cloning: A Laboratory Manual, Cold Spring Harbor Laboratory (1982)), the document (Hitzeman et al., J. Biol. Chem., 255, 12073-12080 (1980)), the document (Luchansky et al Mol. Microbiol. 2, 637-646 (1988)), etc.

The host microorganism that may be used for transformation in the method of the present invention may be prokaryotic or eukaryotic cells. As the prokaryotic cells, any of gram-positive bacteria and gram-negative bacteria may be used. Specific examples thereof may include *Escherichia* genus bacteria, *Salmonella* genus bacteria, *Shigella* genus bacteria, *Enterobacter* genus bacteria, *Serratia* genus bacteria, *Erwinia* genus bacteria, *Serratia* genus bacteria, *Pseudomonas* genus bacteria, *Caulobacter* genus bacteria, *Synechocystis* genus bacteria (e.g. *Synechocystis* species PCC 6803 or *Synechocystis* species PCC 6301), *Synechococcus* genus bacteria, *Bacillus* genus bacteria (e.g. *Bacillus brevis, Bacillus subtilis, Bacillus thuringiensis*, etc.), *Lactococcus* genus bacteria (e.g. *Lactococcus lactis*), *Streptomyces* genus bacteria (e.g. *Streptomyces lividans, Streptomyces ambofaciens, Streptomyces fradiae, Streptomyces griseofuscus*), *Rhodococcus* genus bacteria (e.g. *Rhodococcus erythropolis*), *Corynebacterium* genus bacteria (e.g. *Corynebacterium glutamicum*), *Mycobacterium* genus bacteria (e.g. *Mycobacterium smegmatis*), and the like.

The eukaryotic cells may include yeast cells, examples of which may include *Pichia* genus yeast (e.g. *Pichia pastoris*),

*Saccharomyces* genus yeast (e.g. *Saccharomyces cerevisiae*), *Hansenula* genus yeast (e.g. *Hansenula polymorpha*), *Kluyveromyces* genus yeast (e.g. *Kluyveromyces lactis*), *Schizosaccharomyces* genus yeast (e.g. *Schizosaccharomyces pombe*), etc.

*Escherichia coli* is preferably used. Expression in *Escherichia coli* may provide various advantages in terms of cost and yield compared to other expression host microorganisms. Examples of *Escherichia coli* suitable for use in the expression of the target gene at high yield may include *Escherichia coli* W3110, *Escherichia coli* BL21, BL21 (DE3), DH1, DH41, DH5, DH51, DH51F', DH5IMCR, DH10B, DHIOB/p3, DH1 IS, C600, HB101, JM101, JM105, JM109, JM110, K38, RR1, Y1088, Y1089, CSH18, ER1451, ER1647, NovaBlue, DH5α, K12 RV308, K12 C600, K-12, MG1655, HB101 strain, and the like. Regarding details thereof, reference may be made to the document (Brown, Molecular Biology Labfax, Academic Press (1991)), which is considered part of the present specification.

In order to exhibit and maintain the functions of the target protein in *Escherichia coli*, it is preferable to use *Escherichia coli* with impaired protease activity as a host microorganism. Regarding details thereof, reference may be made to the document (Gottesman, S., Gene Expression Technology: Methods in Enzymology 185, Academic Press, San Diego, Calif., 119-128 (1990)).

Also, in order to realize the expression of the target gene at high yield in *Escherichia coli*, the sequence of the target gene may be optimized with a codon preferred in *Escherichia coli*. With regard thereto, reference may be made to the document (Wada et al., Nucleic Acids Res. 20:2111-2118 (1992)).

In the method of the present invention, the host microorganism transformed above is cultured, thus producing the recombinant protein antigen.

The culture of the transformed host microorganism may be performed through any method known in the art.

As the medium used for cell culture, any of a natural medium and a synthetic medium may be used, so long as it contains a carbon source, a nitrogen source, a trace element, etc. which may be efficiently used by the transformed host microorganism. When animal cells are used as host cells, Eagle's MEM (Eagle's minimum essential medium, Eagle, H. Science 130:432(1959)), α-MEM (Stanner, C. P. et al., Nat. New Biol. 230:52(1971)), Iscove's MEM (Iscove, N. et al., J. Exp.Med. 147:923(1978)), DMEM (Dulbecco's modification of Eagle's medium, Dulbecco, R. et al., Virology 8:396(1959)) or the like is preferably used. Regarding details of the medium, reference may be made to the document [R. Ian Freshney, Culture of Animal Cells, A Manual of Basic Technique, Alan R. Liss, Inc., New York].

Methods of isolating and purifying the target protein are also well known in the art, and any known method may be used. Examples thereof may include ultrafiltration, gel filtration, ion exchange chromatography, affinity chromatography (when labeled peptides are bound), HPLC, hydrophobic chromatography, isoelectric point chromatography, and combinations thereof.

For the production of the target protein of the present invention using recombinant DNA technology, in addition to the description of the present invention, reference may be made to the document [Sambrook et al., Molecular Cloning A Laboratory Manual, Cold Spring Harbor Laboratory Press, US (1989)], the document [Ausubel et al., Current Protocols in Molecular Biology, Jon Willey & Sons, US (1993)], the document [Sambrook, J. & Russell, D., Molecular Cloning, A Laboratory Manual, Cold Spring Harbor Laboratory Press, published in Jan. 15, 2001, vol. 1 7.42 to 7.45, vol. 2 8.9 to 8.17], etc.

Yet another aspect of the present invention pertains to a vaccine composition containing the recombinant protein antigen as an active ingredient.

As used herein, the term "vaccine" refers to the meaning including preventing the infection or re-infection with the corresponding pathogen, reducing the severity of symptoms or eliminating symptoms by the corresponding pathogen, or substantially or completely removing the corresponding pathogen or the disease by the pathogen, by inducing an immune response to the corresponding pathogen in a human host. Thus, the vaccine composition of the present invention may be administered prophylactically to humans before infection with the corresponding pathogen, or may be therapeutically administered to humans after infection with the corresponding pathogen. Here, the term "immune response" includes either or both of a humoral immune response and a cellular immune response.

As used herein, the term "active ingredient" refers to a component that may induce an immune response alone, or may induce an immune response with a carrier that is not itself capable of inducing an immune response. Thus, the active ingredient need not necessarily have immunogenicity (the ability to induce an immune response) by itself. In the present invention, the active ingredient is preferably, but not necessarily, purified. Here, "purified" means that the cellular component of the original organism (i.e. the transformed microorganism in the present invention), in which a subject substance is present, or its culture supernatant component (which is a contaminant), is substantially reduced or eliminated. The state in which the contaminant is substantially reduced or removed means that the purity is at least 50%, preferably at least 90%, and more preferably at least 99%. The purity may be evaluated by methods known in the art, such as chromatography, gel electrophoresis, immunological analysis, etc., and purification methods may be used as known in the art as described below.

As used herein, the term "*tsutsugamushi*" is meant to include all microorganisms classified and identified as *Orientia tsutsugamushi*. Particularly, it includes the Gilliam serotype, the Karp serotype, the Kato serotype and the Boryong serotype.

The vaccine composition of the present invention may be prepared in any suitable and pharmaceutically acceptable formulation. It may be provided in the form of an immediately administrable solution or suspension, or a concentrated crude solution suitable for dilution before administration, or may be provided in a form capable of being reconstituted, such as a lyophilized, freeze-dried, or frozen formulation.

The vaccine composition of the present invention may contain a pharmaceutically acceptable carrier in order to be formulated. The pharmaceutically acceptable carrier for use in the formulation of the vaccine composition is listed and prescribed in the Korean Pharmacopoeia and in foreign pharmacopoeias, especially in the United States, Japan and Europe, and reference may be made to these pharmacopoeias.

The carrier typically includes a diluent, an excipient, a stabilizer, a preservative, and the like. Suitable examples of the diluent may include non-aqueous solvents such as propylene glycol, polyethylene glycol, vegetable oil such as olive oil and peanut oil, or aqueous solvents such as saline (preferably 0.8% saline), water (preferably 0.05 M phosphate buffer) containing a buffer medium, and the like, suitable examples of the excipient may include starch, glucose, lactose, sucrose, gelatin, malt, rice, flour, chalk, silica gel, sodium stearate, glycerol monostearate, talc, sodium chloride, anhydrous skimmed milk, glycerol, propylene, glycol, water, ethanol and the like, and suitable examples of the stabilizer may include carbohydrates such as sorbitol, mannitol, starch, sucrose, dextran, glutamate, and glucose, or proteins such as animal, vegetable or microbial proteins such as milk powder, serum albumin and casein. Suitable examples of the preservative may include thimerosal, merthiolate, gentamicin, neomycin, nystatin, amphotericin B, tetracycline, penicillin, streptomycin, polymyxin B and the like.

The vaccine composition of the present invention may further contain an antigen adjuvant. The antigen adjuvant may be composed of one or more substances that enhance the immune response to the antigen. The adjuvant may function as a tissue reservoir that slowly releases an antigen and/or as a lymphoid system activator that nonspecifically enhances an immune response (Hood et al., Immunology, Second Ed., 1984, Benjamin/Cummings: Menlo Park, Calif., p. 384). Examples of the antigen adjuvant may include complete Freund, incomplete Freund, saponin, gel-type aluminum adjuvants, surface active substances (e.g. lysolecithin, pluronic polyols, polyanions, peptides, oils or hydrocarbon emulsions), vegetable oil (cottonseed oil, peanut oil, corn oil, etc.), vitamin E acetate and the like.

Among antigen adjuvants currently applicable to the human body, an aluminum adjuvant is most widely used, and examples of the aluminum adjuvant may include gel-type aluminum salts such as aluminum phosphate, potassium aluminum sulfate, aluminum hydroxide and the like. The aluminum adjuvant is generally known to elicit a Th2-type immune response and enhance vaccine efficacy (Sokolovska A et al., Vaccine. 2007 Jun. 6; 25(23):4575-85; O'Hagan DT AND Rappuoli R., Pharm Res. 2004 September; 21(9):1519-30). Alhydrogel®, available from InvivoGen, used in Examples of the present invention, is a gel-type colloidal suspension of aluminum hydroxide. Methods of preparing the aluminum adjuvant are known in the art (R. Bomford. Immunological Adjuvants and Vaccines. NATO ASI Series 1989; 179: 35-41; Vogel FR AND Powell MF. Pharm. Biotechnol. 1995; 6: 141-228; Derek T. O'Hagan, Methods in Molecular Medicine. 2000; April 15; 42: 65-90), and the aluminum adjuvant may be used through direct preparation or by purchasing a commercially available product. Examples of commercially available product thereof may include Aluminum hydroxide Gel products made by Sigma and Alhydrogel™ products made by BRENNTAG, in addition to the 2% ALHYDROGEL® made by InvivoGen, used in Examples, which will be described later.

The vaccine composition of the present invention may be produced in an arbitrary unit dose. A unit dose refers to the amount of the active ingredient and the pharmaceutically acceptable carrier contained in each product packaged for use in one or more administrations to a human, and an appropriate amount of such active ingredient and carrier is an amount that may function as a vaccine when inoculation with the vaccine composition of the present invention is performed one or more times, and such an amount may be determined non-clinically or clinically within the ordinary skill of those skilled in the art.

The vaccine composition of the present invention is preferably administered parenterally, for example, rectally, transdermally, intravenously, intraarterially, intramuscularly, intradermally, subcutaneously, intraperitoneally, intraventricularly or the like.

The vaccine composition of the present invention may be administered in a controlled release system. Examples of such a controlled release system may include a liposome, a transplantation osmotic pump, a transdermal patch, and the like. Preferably, the active ingredient is delivered in a liposome manner. Regarding the delivery of the active ingredient in a liposome manner, reference may be made to the document [Langer, Science 249: 1527-1533 (1990)], the document [Treat at al., in Liposomes in the Therapy of Infectious Disease and Cancer, Lopez-Berestein and Fidler (des.), Liss, New York, pp. 353-365 (1989)] and the like. Regarding other active ingredient delivery manners, reference may be made to the document [Langer, supra; Sefton, CRC Crit. Ref. Biomed. Eng. 14:201 (1987)], the document [Buchwald et al., Surgery 88: 507 (1980)], the document [Saudek et al., N. Engl. J. Med. 321:574 (1989)], the document [Medical Applications of Controlled Release, Langer and Wise (eds.), CRC Pres., Boca Raton, Fla. (1974)], the document [Controlled Drug Bioavailability. Drug Product Design and Performance, Smolen and Ball (eds.), Wiley, New York (1984)], the document [Ranger and Peppas, J. Macromol. Sci. Rev. Macromol. Chem. 23:61 (1983)], the document [During et al., Ann. Neurol. 25:351 (1989)], the document [Howard et al., J. Neurosurg. 71:105 (1989)] and the like. These documents are considered part of the present specification.

The dose of the vaccine composition of the present invention may be determined by a medical practitioner in consideration of patient characteristics such as age, weight, gender, symptoms, complications, and the incidence of other diseases.

Further, the temporal interval of administration and the number of administrations may be determined in consideration of the dosage form that is used, the half-life of the active ingredient in the blood, and the like.

Although the dose, the temporal interval and the number of administrations should be determined depending on the judgment of the medical practitioner or the individual, an appropriate dose will be usually determined within the range of about 0.1 to 10 mg for 1 kg of body weight per day at an administration interval of 3 to 10 days, the number of administrations ranging from 1 to 5.

Still yet another aspect of the present invention pertains to a composition for detecting a *tsutsugamushi*-specific antibody, comprising the recombinant protein antigen.

The detection composition of the present invention serves to detect a *tsutsugamushi*-specific antibody, especially a TA56 antigen-specific antibody, in a biosample, and the composition of the present invention is able to distinguish *tsutsugamushi*-infected and uninfected persons from each other by bringing the same into contact with a biosample and measuring the extent of reaction therebetween. In particular, this composition may be useful to distinguish whether or not a patient with symptoms identical or similar to those of *tsutsugamushi* disease is infected with *tsutsugamushi* during the period of risk of onset of *tsutsugamushi* disease.

As used herein, the term "specific binding" means that the recombinant protein antigen, specifically binding to a *tsutsugamushi*-specific antibody, especially a TSA56 antigen-specific antibody, binds only to the antibody and does not substantially bind to other proteins. Here, the term "substantially" means that nonspecific binding, the extent of which is low, may occur, and such nonspecific binding may be removed by washing using a washing solution before detection of specific binding as described below.

As used herein, the term "biosample" refers to a sample in which a *tsutsugamushi*-specific antibody, especially a TSA56 antigen-specific antibody, may exist, and includes the blood, serum, plasma, saliva, tears, mucus, snot, vaginal discharge, and the like, and preferably serum. This is because it is known in the art that the antibody is present at a high concentration in the serum.

The composition of the present invention may be configured such that the recombinant protein antigen is in the form of being dissolved in a soluble solution, for example, a carbonate buffer solution or a bicarbonate buffer solution, or in a lyophilized form.

The composition of the present invention may be used in the state of being fixed to a support, and examples of the solid support that may be used may include, but are not limited to, particles (resin beads, magnetic beads, metal microparticles, gold colloids, etc.), substrates (microtiter plates, glass substrates, silicon substrates, resin substrates, electrode substrates, membranes, etc.), and the like. Examples of the material for the support may include (i) inorganic materials such as glass, quartz glass, alumina, sapphire, forsterite, silicon oxide and the like, and (ii) organic materials such as polyethylene, polyvinyl acetal, acrylic resin, polycarbonate, phenol resin, urea resin, epoxy resin, melamine resin, silicone resin, polyphenylene oxide, polysulfone, polyethylene glycol, agarose, acrylamide, nitrocellulose, nylon, latex, and the like.

A method of fixing the composition of the present invention to the support may include direct fixation through adsorption (e.g. coating) or indirect fixation using a linker that binds both to the protein and the support.

When the composition of the present invention is used in the state of being adsorbed to the support, such adsorption may be implemented in a manner in which the composition of the present invention is diluted with a 0.06 M carbonate buffer solution or bicarbonate buffer solution having a pH of 9.5 and the diluted solution is brought into contact with the support at a predetermined temperature for a predetermined time. Here, the time and temperature for adsorption are not particularly limited, so long as sufficient adsorption occurs. For example, upon adsorption at 4° C., the process may be performed for 72 hr, and for example, upon adsorption at 37° C., the process may be performed for 2 hr. After adsorption, washing may be conducted using distilled water or ethanol, and coating may be performed using a blocking agent such as bovine serum albumin (BSA) contained in a solution such as PBS. After coating using the blocking agent, washing may be performed using distilled water or a buffer solution containing no blocking agent.

When the support is treated with a biosample, the composition of the present invention (particularly the recombinant protein antigen contained in the composition) adsorbed to the support is able to form a complex with a *tsutsugamushi*-specific antibody, especially a TSA56-specific antibody, contained in the biosample. After induction of the complex formation, in order to remove nonspecifically bound antibodies or contaminants, washing is preferably performed using a washing buffer such as TWEEN-20 or a washing agent such as distilled water.

The complex may be detected through any of various methods, whereby the presence or absence and/or the concentration of a *tsutsugamushi*-specific antibody, especially a TSA56-specific antibody, in the biosample may be qualitatively and quantitatively determined. This will provide useful information as to whether the subject is infected with *tsutsugamushi*.

The complex may be detected using a detection agent, and the detection agent may be, for example, a secondary antibody binding to a *tsutsugamushi*-specific antibody, especially a TSA56-specific antibody. Examples of the secondary antibody may include those that recognize the Fc portion of the antibody (primary antibody), and the secondary antibody may be obtained by immunizing an animal such as a bird (e.g. chicken, etc.), a mammal (e.g. rabbit, goat, horse, sheep, rat, etc.), and the like with the Fc portion and performing isolation and purification from the blood of the animal.

The secondary antibody may be conjugated with a label or an enzyme that provides a detection signal, thus facilitating detection.

Label conjugation serves to bind any label capable of providing a detection signal to the antibody. Examples of the label may include radioisotopes such as tritium, iodine ($^{131}$I, $^{125}$I, $^{123}$I, $^{121}$I), phosphorus ($^{32}$P), sulfur ($^{35}$S), metals (e.g. $^{68}$Ga, $^{67}$Ga, $^{68}$Ge, $^{54}$Mn, $^{99}$Mo, $^{99}$Tc, $^{133}$Xe) and the like, fluorescence substances or fluorophores such as fluorescein isothiocyanate, tetramethyl rhodamine isothiocyanate, substituted rhodamine isothiocyanate, dichlorotriazine isothiocyanate, Alexa or AlexaFluoro, and the like.

Enzyme conjugation serves to bind an enzyme such as peroxidase (POD), alkaline phosphatase, β-galactosidase, urease, catalase, glucose oxidase, lactate dehydrogenase, amylase or a biotin-avidin complex to the antibody, and these enzymes provide a certain detection signal when reacting with a certain substrate. For example, peroxidase shows a purple color when reacting with aminosalicylic acid and hydrogen peroxide or p-phenylenediamine and hydrogen peroxide, alkaline phosphatase shows a yellow color when reacting with dinitrophenylphosphate, and β-galactosidase shows a purple color when reacting with O-nitrophenyl-β-D-galactopyranoside.

The label or enzyme is preferably covalently bonded to the antibody.

Upon detection using the detection agent such as the secondary antibody or the like, the extent of reaction of the secondary antibody with the complex may be measured through a variety of immunoassay methods well known or publicly known in the art, such as enzyme immunoassay, fluorescence immunoassay, radioimmunoassay, luminescence immunoassay, and the like. Preferably enzyme immunoassay, and most preferably ELISA (enzyme-linked immunosorbent assay) is used.

A further aspect of the present invention pertains to a kit for detecting a *tsutsugamushi*-specific antibody, especially a TSA56 antigen-specific antibody.

The detection kit of the present invention includes the aforementioned recombinant protein antigen.

The recombinant protein antigen contained in the kit of the present invention may be provided in the form of being attached to or detached from a support, or may be provided in a dissolved form in a soluble solution or in a lyophilized form.

The kit of the present invention may further include a detection agent for detecting a complex of the *tsutsugamushi*-specific antibody, especially the TSA56 antigen-specific antibody, in the biosample and the recombinant protein antigen specifically binding to the specific antibody. The detection agent may be a secondary antibody conjugated with the label or enzyme described above.

Furthermore, the kit of the present invention may further include a carrier, a washing buffer, a diluted sample solution, an enzyme substrate, and a reaction stop solution, and may also include instructions to teach the method of use, including a method of analysis of the results, etc.

Still a further aspect of the present invention pertains to a method of detecting a *tsutsugamushi*-specific antibody, especially a TA56 antigen-specific antibody, in a biosample.

The method of the present invention includes (a) coupling a biosample with the composition for detecting a *tsutsugamushi*-specific antibody including the recombinant protein antigen to afford a complex of the *tsutsugamushi*-specific antibody, especially the TA56 antigen-specific antibody, in the biosample and the recombinant protein antigen specifically binding to the specific antibody, and (b) detecting the complex.

In the method of the present invention, the biosample in step (a) is preferably serum for the reasons described above.

Also in the method of the present invention, the detecting the complex in step (b) includes reacting a secondary antibody conjugated with a label or an enzyme capable of providing a detection signal with the complex and measuring the extent of reaction with the complex. The extent of reaction of the secondary antibody with the complex may be measured through enzyme immunoassay, fluorescence immunoassay, radioimmunoassay, luminescence immunoassay, etc., as described above. Preferably, ELISA (enzyme-linked immunosorbent assay) is used.

Yet a further aspect of the present invention pertains to a method of providing useful information for the diagnosis of infection with *tsutsugamushi*.

The method of the present invention includes the same steps as the method of detecting the *tsutsugamushi*-specific antibody in the biosample described above, and thus the description of the detection method above is applied as it is to the method of the present invention.

Advantageous Effects

As described hereinbefore, the present invention can provide a novel recombinant protein antigen derived from the conserved sequence of a TSA56 antigen, which can be useful in the diagnosis of infection with *tsutsugamushi* and as a vaccine for *tsutsugamushi*.

The novel recombinant protein antigen of the present invention can be expected to provide a vaccine composition and a diagnostic composition capable of overcoming the difference in the ability to induce protective immunity and the difference in diagnostic ability depending on the different genotypes.

BRIEF DESCRIPTION OF DRAWINGS

FIGS. 3, 4, 5, 6, 7, and 8 show respective amino acid sequences of seven conserved blocks derived from each of 17 genotypes;

FIGS. 9 and 10 show respective amino acid sequences of seven conserved blocks derived from each of 5 genogroups;

FIG. 11 shows respective amino acid sequences of seven conserved blocks of a representative sequence;

FIG. 12 shows the amino acid sequence of cTSA56_Boryong used as a vaccine antigen;

FIG. 14 shows the results of IgG1 and IgG2c antibody titers specific to a TSA56_Boryong protein induced after immunization of mice with the recombinant protein three times.

DETAILED DESCRIPTION

A better understanding of the present invention will be given through the following examples. However, these examples are not to be construed as limiting the scope of the present invention.

<Example 1> Identification of Conserved Blocks of TSA56 and Preparation of cTSA56 Recombinant Protein Antigen 1030 tsa56 gene sequences published before Dec. 31, 2015 were collected from the base sequence database of the National Center for Biotechnology Information. Of these, 206 gene sequences, among 324 sequences including 85% or more of the site encoding the entire TSA56 protein, were selected (in the tsa56 gene sequences listed in the National Center for Bioinformatics, sequences containing the entire ORF and only a part thereof are present, and thus, among these gene sequences, genes including a site encoding an amino acid sequence having 85% or more correspondence with the entire TSA protein amino acid sequence of the corresponding strain are selected).

The selected 206 tsa56 genes were converted to amino acid sequences, followed by multiple sequence alignment using an MAFFT algorithm program (Multiple Alignment using Fast Fourier Transform; Molecular Biology and Evolution, 2013, 30, 772-780). The protein-coding sections, which are contained in common in the 206 genes, were converted to base sequences and used to construct the phylogenetic tree.

Figure 1:
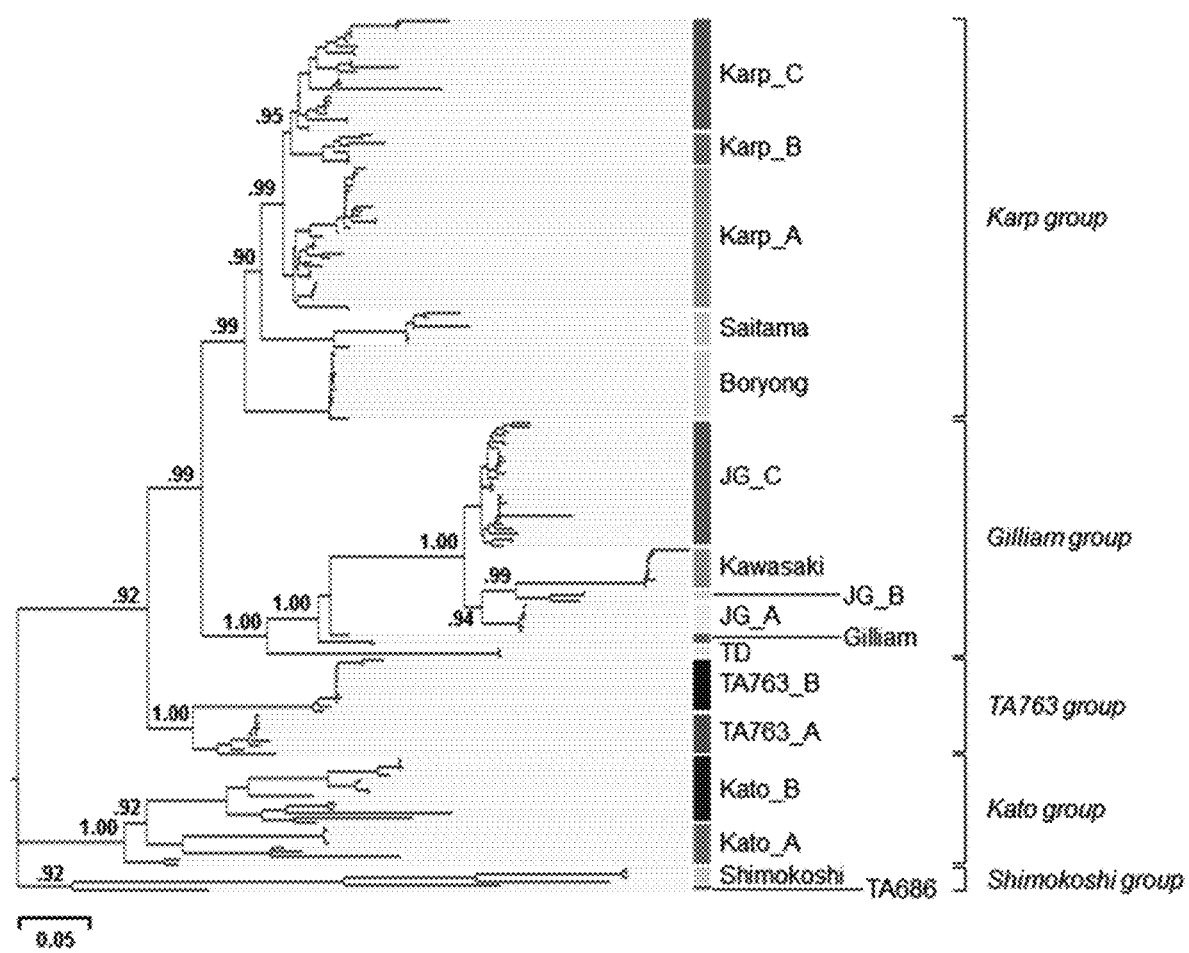
FIG. 1 shows the results of phylogenetic tree analysis of 206 tsa56 genes collected and the genotype classification results depending thereon.
Figure 2:
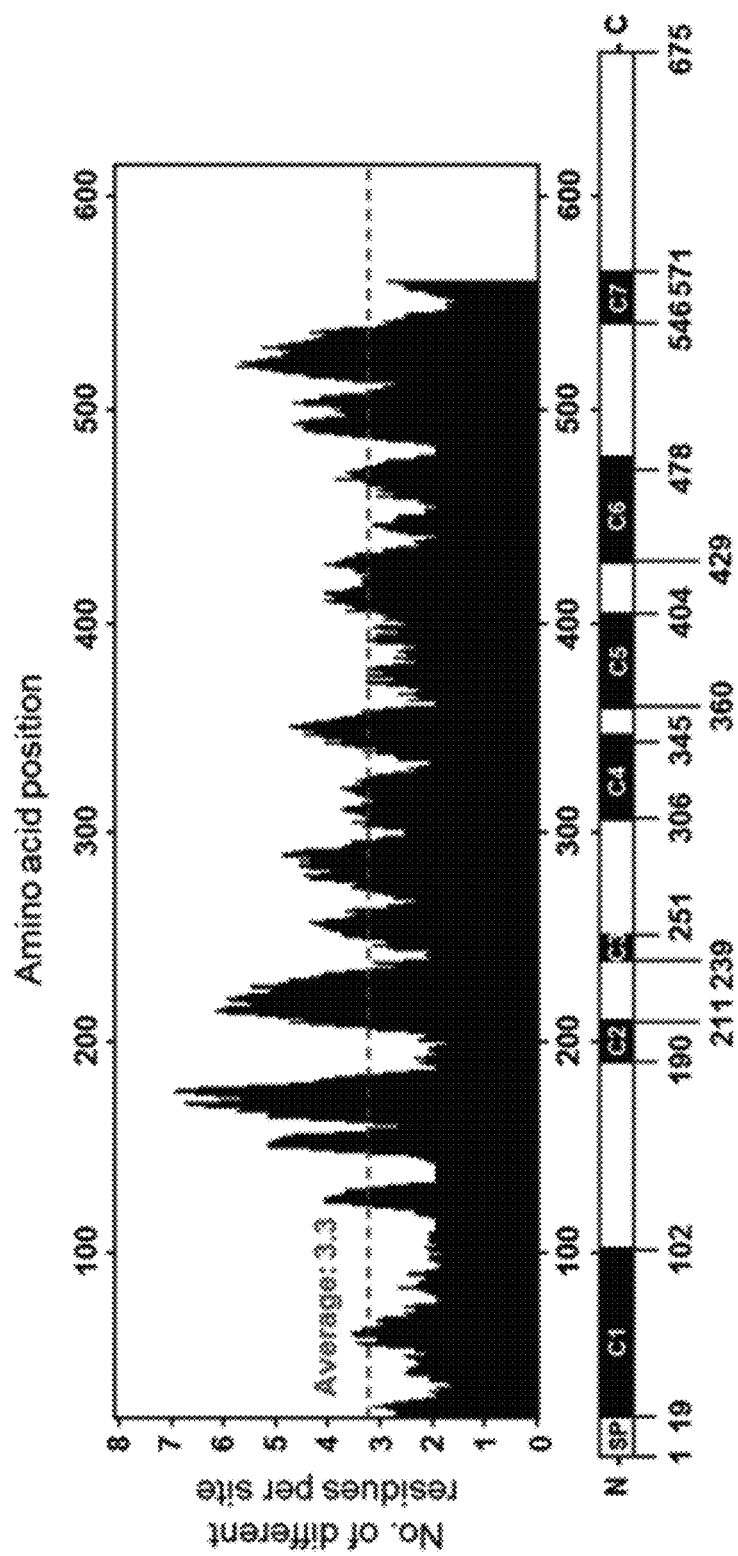
FIG. 2 shows seven conserved blocks (C1 to C7) identified through amino acid sequence analysis of 206 TSA56 proteins.

In order to construct the phylogenetic tree, base sequences were corrected with an optimized substitution matrix using a jModelTest 2.0 program (Darriba D, Taboada GL, Doallo R, Posada D. 2012. jModelTest 2: more models, new heuristics and parallel computing. Nature Methods 9(8), 772; Guindon S and Gascuel O (2003). A simple, fast and accurate method to estimate large phylogenies by maximum-likelihood, Systematic Biology 52: 696-704). The gene phylogenetic tree was constructed through a SeaView 4.5.1 program based on, as a kind of Maximum Likelihood, RaxML (Randomized Axelerated Maximum Likelihood, BIOINFORMATICS APPLICATIONS NOTE Vol. 22 no. 21 2006, pages 2688-690), and these sequences were classified into 17 genotypes with a statistically significant difference (support value=0.9) through a Shimodaira-Hasegawa-like (SH-like) test (Molecular Biology and Evolution, 2010, 27, 221-224), which were then further classified into 5 genogroups based on the distances therebetween in the phylogenetic tree [FIG. 1]. In order to define the sections in which amino acid sequences of the 206 genes were conserved, the arithmetic average value of amino acid mutations of genes for each section sequence comprising 10 consecutive amino acids in individual positions of the amino acid sequences (e.g. the first amino acid forms a section with the next 9 amino acids, and the second amino acid forms a section with the next 9 amino acids) was calculated, thus obtaining the overall average value of 3.3 amino acid mutations/site, and the sections in which the number of amino acid mutations was kept below the above average value were determined among sections comprising 10 consecutive amino acids in individual positions of the amino acid sequences. Next, using a Gblocks program (Systematic biology, 2007, 56, 564-577), conserved sites having a small difference in consecutive amino acid sequences among genes and having high consistency were determined. Using these two methods, seven conserved blocks having a relatively small difference in the genes were determined [FIG. 2]. The amino acid sequences of the conserved blocks of 17 genotypes and 5 genogroups derived from the main amino acid conserved sequences (major consensus sequences) of 206 genes and a representative sequence (universal conserved sequence) representing the entire sequence are summarized in [FIG. 3] to [FIG. 11].

The results of comparison of sequence homology of the representative sequence (the sequence in which C1 to C7 are connected in order) and the remaining 22 sequences are shown in [Table 1] below.

TABLE 2

Results of comparison of sequence homology of representative sequence and remaining sequences

| Genotype | Sequence homology with representative sequence (%) |
|---|---|
| Karp_C con | 94.5 |
| Karp_B con | 91.9 |
| Karp_A con | 92.3 |
| Saitama con | 85.6 |
| Boryong con | 88.2 |
| JG_C con | 92.3 |
| Kawasaki con | 89.7 |
| JG_B con | 89.3 |
| JG_A con | 92.3 |
| Gilliam con | 92.3 |
| TD con | 87.1 |
| TA763_B con | 88.9 |
| TA763_A con | 91.9 |
| Kato_B con | 91.9 |
| Kato_A con | 90 |
| Shimokoshi con | 72.7 |
| TA686 con | 87.5 |
| Karp group con | 94.5 |
| Gilliam group con | 94.1 |
| TA763 group con | 92.6 |
| Kato group con | 93.4 |
| Shimokoshi group con | 76.4 |
| Universal TSA56 con | 100 |

In order to evaluate the likelihood of use of the recombinant protein antigens comprising the amino acid sequences of a total of 23 conserved blocks (protein antigens comprising conserved block sequences connected in order) for diagnosis and as a vaccine, the protein of the sequence resulting from connecting seven conserved block sequences of the Boryong genotype as a typical example, as shown in [FIG. 4] ("cTSA56_Boryong") and the protein of the representative sequence (universal conserved TSA56; "ucTSA56") were used for experiments. The sequences of C1 to C7 of cTSA56_Boryong were obtained by extracting the sequences of amino acids having the highest frequency from amino acid sequences corresponding to the seven conserved sites of 17 genes identified as Boryong genotype among 206 genes. The sequence of cTSA56_Boryong is shown in [FIG. 12] (and SEQ ID NO: 24) and the amino acid sequence of cTSA56_Boryong shown in [FIG. 12] resulted from removing the amino acid sequence of "LSLTTGLPFGGTLAAGMTIA" (SEQ ID NO: 25) from the Boryong genotype conserved block 1 (C1) amino acid sequence of [FIG. 4], and this amino acid sequence was excluded because it was predicted to constitute a transmembrane motif and also because it was confirmed to inhibit the production of the recombinant protein, thereby preparing a recombinant antigen protein. ucTSA56 is a sequence composed of amino acids at positions having the highest frequency among the amino acid sequences included in seven conserved blocks of the genes included in 17 genotypes, and the corresponding sequence is shown in [FIG. 11] and SEQ ID NO: 23.

The nucleic acid sequence encoding cTSA56_Boryong or ucTSA56 was chemically synthesized, amplified through PCR, cloned into a pET-28a(+) plasmid as an *Escherichia coli* expression vector, and introduced into *Escherichia coli* BL21(DE3). The recombinant *Escherichia coli* was cultured in a Kanamycin (50 µg/mL)-containing LB broth until OD600 nm (Optical Density 600 nm) reached 0.6-0.8. Then, a 0.1 mM isopropyl β-D-thiogalactoside (IPTG) was added thereto and then cultured at 16° C. for 18 hr, thus inducing the expression of a protein.

After termination of induction of expression, the bacteria were centrifuged at 1,000×g for 10 min, suspended in a Ni-nitrilotriacetic acid (NTA) His-binding buffer solution (300 mM NaCl, 50 mM sodium phosphate buffer, 10 mM imidazole) containing 1 mg/mL lysozyme, and reacted at 4° C. for 30 min. Thereafter, sonication on ice was performed for 5 min, and the resulting lysate was centrifuged at 1,600×g at 4° C. for 20 min.

The supernatant was collected and reacted at 4° C. for 60 min with a Ni-nitrilotriacetic acid (NTA) His-binding resin pre-equilibrated with a binding buffer solution.

The resin was washed with a binding buffer solution containing 50 mM imidazole, and the protein was then purified with a binding buffer solution containing 250 mM imidazole. Thereafter, in order to remove free imidazole, dialysis was conducted at 4° C. for 18 hr in a phosphate buffer solution (pH 7.4), and in order to remove endotoxins from the purified protein, an endotoxin removal resin was used. The removal of the endotoxin to the level of EU<0.05/dose from the purified protein solution was confirmed through LAL (limulus amebocyte lysate) assay.

Figure 13:
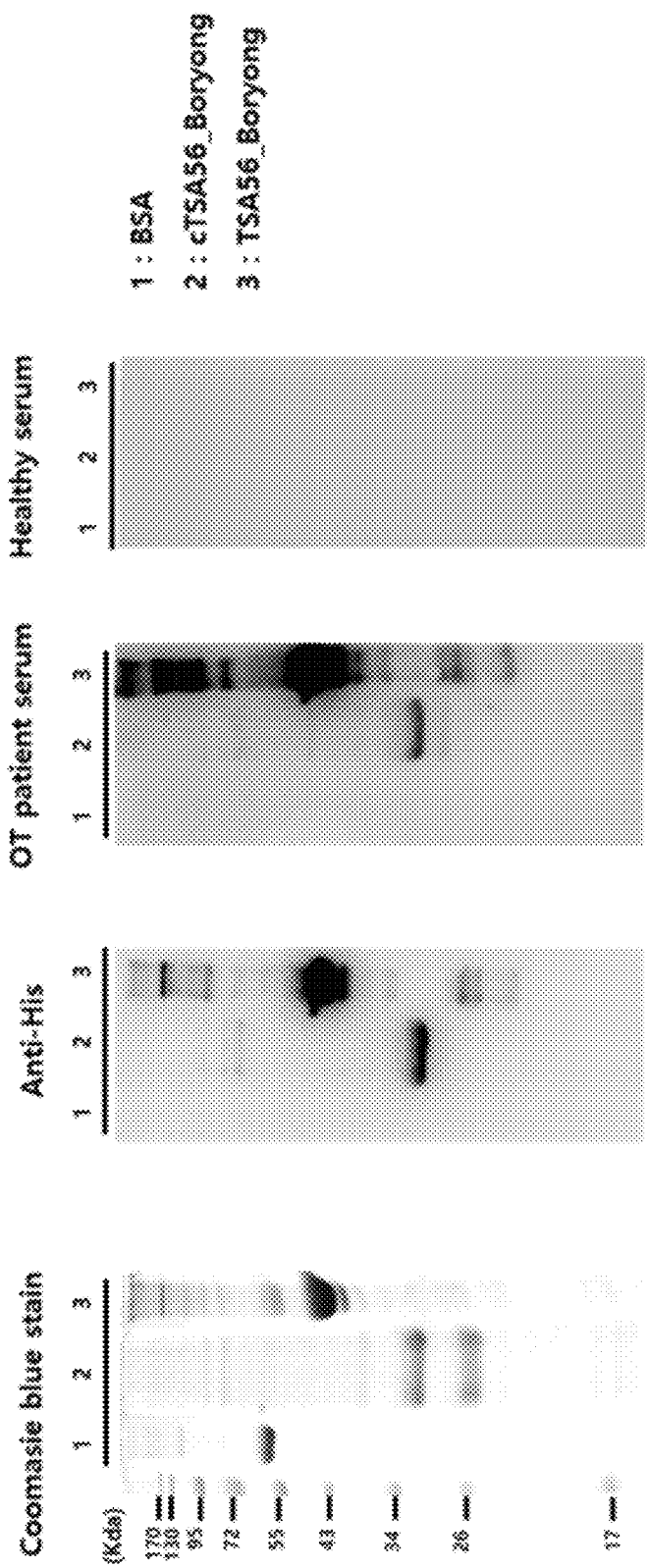
FIG. 13 shows the Coomassie blue staining results of a purified cTSA56_Boryong recombinant protein and a TSA56_Boryong recombinant protein and the western blotting results using the antiserum of a healthy person and a *tsutsugamushi*-infected patient.

The results of Coomassie blue staining after electrophoresis of the extracted protein and the results of western blotting for the reaction of the *tsutsugamushi* disease patient serum and the anti-His antibody are shown in [FIG. 13]. As is apparent from the results of [FIG. 13], a cTSA56_Boryong recombinant protein having a molecular weight of 30 kDa was obtained as expected, and the cTSA56_Boryong recombinant protein did not react with the healthy serum but reacted with the *tsutsugamushi*-infected patient (OT patient) serum and thereby was useful in the diagnosis of a *tsutsugamushi*-infected patient.

<Example 2> Verification of Immunogenicity and Vaccine Efficacy Using cTSA56_Boryong Recombinant Protein Antigen 1. Recombinant Protein Antigen Immunization and Blood Collection 20 µg of the purified cTSA56_Boryong recombinant protein, 20 µg of TSA56_Boryong (a control, excluding an extracellular site of Boryong genotype TSA56 protein, namely a signal peptide and a transmembrane domain), and a phosphate buffer solution as a negative control were used for immunization. Each vaccine formulation was mixed with a phosphate buffer solution so that the total amount was 80

µL, and was added with 20 µL of 2% ALHYDROGEL as an immune adjuvant so that the final volume ratio was 4:1 (antigen:immune adjuvant), followed by reaction at room temperature for 15 min.

Each vaccine formulation thus obtained was subcutaneously injected into C57BL/6 (6- to 8-week-old female) mice, and immunization was carried out a total of three times at intervals of two weeks.

Seven days after each immunization, blood was collected through orbital blood collection, and the serum was separated through centrifugation for 5 min at 2500×g.

2. ELISA for Quantifying Specific Antibody

The purified TSA56_Boryong protein was diluted to a concentration of 1 µg/mL with a 0.05 M bicarbonate buffer (pH 9.5) and an immunoassay plate was coated with 100 µL thereof per well at 4° C. for 18 hr.

The coated wells were washed using a washing solution (0.05% Phosphate-Buffered Saline TWEEN-20, PBST), and blocked using 3% BSA (bovine serum albumin) at room temperature for 2 hr.

A 100-fold-diluted solution of the mouse serum was subjected to 2-fold serial dilution, added in an amount of 100 µL/well, and reacted at room temperature for 1 hr.

Washing was performed using a washing solution (0.05% Phosphate-Buffered Saline TWEEN-20, PBST), after which each of 10000-fold-diluted anti-mouse-IgG1 and IgG2c HRP conjugates was added in an amount of 100 µL/well, and reacted at room temperature for 1 hr.

Washing was performed using a washing solution (0.05% Phosphate-Buffered Saline TWEEN-20, PBST), after which a color-developing agent 3,3',5,5'-tetramethylbenzidine (TMB) solution was added in an amount of 100 µL/well, and reacted at room temperature for 7 min.

A reaction stop solution (1N $H_2SO_4$) was added in an amount of 100 µL/well, after which the absorbance was measured at 450 nm using a microplate reader.

Figure 14:
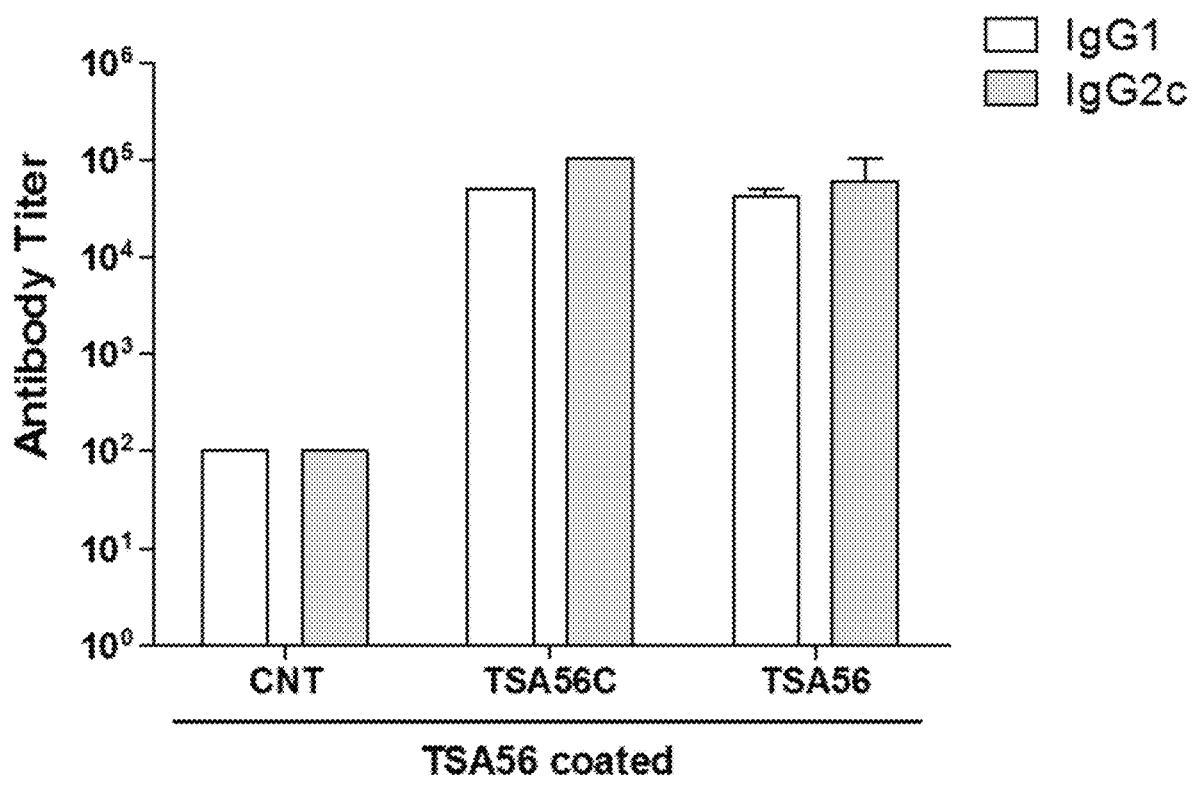

In the cTSA56_Boryong recombinant protein and TSA56_Boryong protein immunization test groups, except for the phosphate buffer group as the negative control, the IgG1 and IgG2c antibody titers specific to TSA56_Boryong were confirmed to be increased almost identically [FIG. 14].

3. Mouse Infection Test

As described above, each vaccine formulation was subcutaneously injected into C57BL/6 (6- to 8-weak-old female) mice (n=5/group), and immunization was carried out a total of three times at intervals of two weeks. After seven days, the immunized mice were intraperitoneally infected with Boryong or Karp genotype *tsutsugamushi* in an amount corresponding to 100 times the half-lethal dose (100×LD50). After infection, the survival rate of the mice was observed for 30 days.

Figure 15:
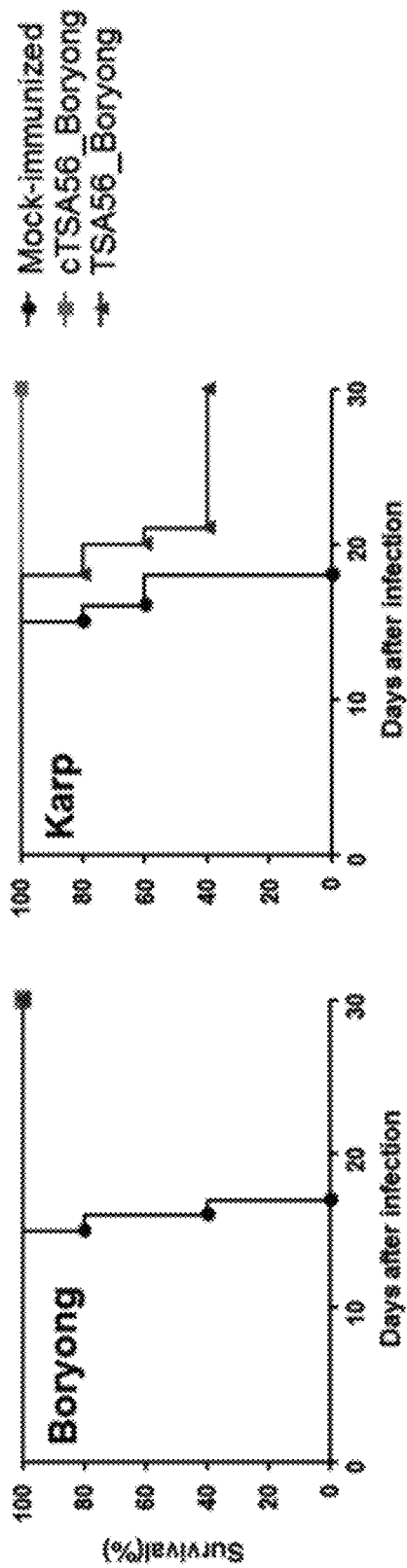
FIGS. 15 and 16 show the results of survival rate analysis of immunized mice after *tsutsugamushi* infection.

All of the mice immunized with TSA56_Boryong or cTSA56_Boryong recombinant protein survived after Boryong genotype infection. In the case of Karp genotype infection, only 40% of the mice immunized with TSA56_Boryong survived, but all of the mice immunized with cTSA56_Boryong survived. All mice died in the negative control not immunized with the antigen. Therefore, it can be confirmed that protective immunity was induced for the same genotype through cTSA56_Boryong recombinant protein immunization and also that further improved protective immunity was provided for other genotypes. The results are shown in [FIG. 15].

<cTSA56_Boryong Recombinant Protein Antigen>

The cTSA56_Boryong or TSA56_Boryong vaccine formulation of Example was subcutaneously injected into C57BL/6 (6- to 8-week-old, female) mice (n=5/group), and immunization was carried out a total of three times at intervals of two weeks. After seven days, the immunized mice were intraperitoneally infected with Boryong or Karp genotype *tsutsugamushi* in an amount corresponding to 100 times the half-lethal dose (100×LD50). After infection, the survival rate of the mice was observed for 30 days.

All of the mice immunized with TSA56_Boryong or cTSA56_Boryong recombinant protein survived after Boryong genotype infection. In the case of Karp genotype infection, only 40% of the mice immunized with TSA56_Boryong survived, but all of the mice immunized with cTSA56_Boryong survived. All mice died in the negative control not immunized with the antigen. Therefore, it can be confirmed that protective immunity was induced for the same genotype through cTSA56_Boryong recombinant protein immunization and also that further improved protective immunity was provided for other genotypes. The results are shown in [FIG. 15].

<ucTSA56 Recombinant Protein Antigen>

A ucTSA56 recombinant protein antigen was injected into C57BL/6 (6- to 8-week-old, female) mice (n=5/group), and the effect thereof on the mouse survival rate was evaluated in the same manner as in Example above. As a control, TSA56_Boryong was used.

Figure 16:
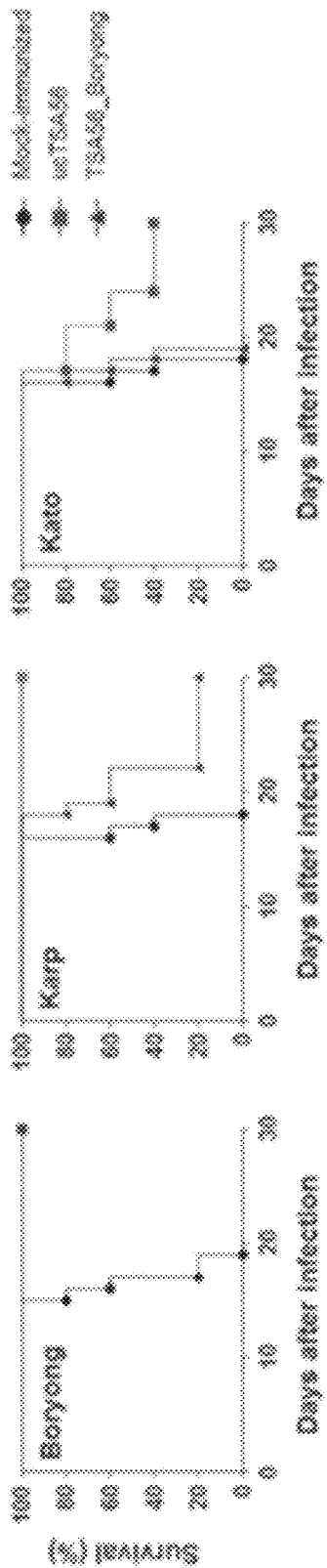

Consequently, all of the mice immunized with TSA56_Boryong or ucTSA56 recombinant protein survived after Boryong genotype infection. In the case of Karp genotype infection, only 20% of the mice immunized with TSA56_Boryong survived, but all of the mice immunized with ucTSA56 survived. In the case of Kato genotype infection, all of the mice immunized with TSA56_Boryong died, but 40% of the mice immunized with ucTSA56 survived. All mice died in the negative control not immunized with the antigen. Therefore, it can be confirmed that further improved protective immunity was provided for a variety of genotypes through ucTSA56 recombinant protein immunization. The results are shown in [FIG. 16].

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A recombinant protein antigen of *Orientia tsutsugamushi* having a sequence homology of 90% or more with SEQ ID NO 23.

2. A recombinant protein antigen of claim 1, the antigen having the sequence of SEQ ID NO: 23.

3. A gene encoding the recombinant protein antigen of claim 1.

4. A method of preparing a recombinant protein antigen of *Orientia tsutsugamushi* having a sequence homology of 90% or more with SEQ ID NO: 23, the method comprising: (i) preparing an expression vector containing the gene of claim 3, (ii) transforming the expression vector into a host cell, (iii) culturing the transformed host cell, and (iv) isolating and purifying the recombinant protein antigen from a resultant culture broth.

5. A vaccine composition for *Orientia tsutsugamushi*, containing the recombinant protein antigen of claim 1 as an active ingredient.

6. The vaccine composition of claim 5, wherein the composition contains a pharmaceutically acceptable carrier.

7. The vaccine composition of claim 6, wherein the pharmaceutically acceptable carrier includes at least one selected from the group consisting of a diluent, an excipient, a stabilizer and a preservative.

8. The vaccine composition of claim 5, wherein the composition further contains an antigen adjuvant.

9. The vaccine composition of claim 8, wherein the antigen adjuvant is a gel-type aluminum salt.

10. A composition for detecting an *Orientia tsutsugamushi*-specific antibody, the composition comprising the recombinant protein antigen of claim 1.

11. The composition of claim 10, wherein the *Orientia tsutsugamushi*-specific antibody is a TSA56 antigen-specific antibody.

12. A kit for detecting an *Orientia tsutsugamushi*-specific antibody, the kit comprising the recombinant protein antigen of claim 1.

13. The kit of claim 12, wherein the kit further comprises a detection agent for detecting a complex of a *Orientia tsutsugamushi*-specific antibody in a biosample and the recombinant protein antigen of claim 1 specifically binding to the specific antibody.

14. The kit of claim 12, wherein the detection agent is a secondary antibody conjugated with a label or an enzyme.

15. The kit of claim 12, wherein the kit further comprises at least one selected from among a carrier, a washing buffer, a diluted sample solution, an enzyme substrate, a reaction stop solution and instructions to teach a method of use thereof.

16. A method of detecting an *Orientia tsutsugamushi*-specific antibody in a biosample, the method comprising:

(a) reacting a biosample with a composition for detecting a *Orientia tsutsugamushi*-specific antibody including the recombinant protein antigen of claim 1 to afford a complex of the *Orientia tsutsugamushi*-specific antibody in the biosample and the recombinant protein antigen of claim 1 specifically binding to the specific antibody, and (b) detecting the complex.

17. The method of claim 16, wherein the *Orientia tsutsugamushi*-specific antibody is a TSA56 antigen-specific antibody.

18. The method of claim 16, wherein the biosample is serum.

19. The method of claim 16, wherein the detecting the complex in step (b) includes reacting a secondary antibody conjugated with a label or an enzyme capable of providing a detection signal with the complex and measuring an extent of reaction with the complex.

* * * * *

SEQUENCE LISTING

<160> NUMBER OF SEQ ID NOS: 25

<210> SEQ ID NO 1
<211> LENGTH: 271
<212> TYPE: PRT
<213> ORGANISM: Artificial Sequence
<220> FEATURE:
<223> OTHER INFORMATION: Karp_C -continued

<400> SEQUENCE: 1

Ser Ala Ser Ala Ile Glu Leu Gly Asp Glu Gly Gly Leu Glu Cys Gly
1               5                   10                  15

Pro Tyr Ala Lys Val Gly Val Gly Gly Met Ile Thr Gly Val Glu
            20                  25                  30

Ser Thr Arg Leu Asp Pro Ala Ala Asp Gly Lys Lys His Leu Ser
        35                  40                  45

Leu Thr Thr Gly Leu Pro Phe Gly Gly Thr Leu Ala Ala Gly Met Thr
    50                  55                  60

Ile Ala Pro Gly Phe Arg Ala Glu Leu Gly Val Met Tyr Leu Thr Asn
65                  70                  75                  80

Ile Lys Leu Thr Pro Pro Gln Pro Thr Ile Met Pro Ile Ser Ile Ala
                85                  90                  95

Asp Arg Asp Phe Gly Ile Asp Arg Ile Ala Trp Leu Lys Asn Cys Ala
            100                 105                 110

Gly Ile Asp Tyr Trp Arg His Leu Val Val Gly Leu Ala Ala Leu Ser
            115                 120                 125

Asn Ala Asn Lys Pro Ser Ala Ser Pro Val Lys Val Leu Ser Asp Lys
        130                 135                 140

Ile Thr Gln Ile Tyr Ser Asp Ile Lys Leu Pro Asn Ser Ala Ser Val
145                 150                 155                 160

Glu Gln Ile Gln Asn Lys Met Gln Glu Leu Asn Asp Val Leu Glu Glu
                165                 170                 175

Leu Arg Asp Ser Phe Asp Gly Tyr Ile Ser Asn Ala Phe Ala Asn Gln
            180                 185                 190

Ile Gln Leu Asn Phe Gln Ala Thr Ala Gln Glu Ala Val Ala Ala
        195                 200                 205

Ala Val Arg Leu Leu Asn Gly Asn Asp Gln Ile Ala Gln Leu Tyr Lys
    210                 215                 220

Asp Leu Val Lys Leu Gln Arg His Ala Gly Ile Lys Lys Ala Met Glu
225                 230                 235                 240

Lys Leu Ala Ala Gln Glu Ala Glu Phe Asp Leu Ser Met Ile Val Gly
                245                 250                 255

Gln Val Lys Leu Tyr Ala Asp Val Met Thr Thr Glu Ser Phe Ser
            260                 265                 270

<210> SEQ ID NO 2
<211> LENGTH: 272
<212> TYPE: PRT
<213> ORGANISM: Artificial Sequence
<220> FEATURE:
<223> OTHER INFORMATION: Karp_B

<400> SEQUENCE: 2

Ser Ala Ser Ala Ile Glu Leu Gly Asp Glu Gly Gly Leu Glu Cys Gly
1               5                   10                  15

Pro Tyr Gly Lys Val Gly Ile Val Gly Gly Met Ile Thr Gly Val Glu
            20                  25                  30

Ser Thr Arg Leu Asp Ser Ala Asp Ala Glu Gly Lys Lys Arg Leu Pro
        35                  40                  45

Leu Thr Thr Ser Met Pro Phe Gly Gly Thr Leu Ala Ala Gly Met Thr
    50                  55                  60

Ile Ala Gln Gly Phe Arg Ala Glu Leu Gly Val Met Tyr Leu Thr Asn
65                  70                  75                  80

Ile Lys Leu Thr Pro Pro Gln Pro Thr Ile Met Pro Ile Ser Ile Ala

```
                        85                  90                  95
Asp Arg Asp Phe Gly Ile Asp Arg Ile Ala Trp Leu Lys Asn Tyr Ala
                100                 105                 110
Gly Ile Asp Tyr Trp Arg His Leu Val Val Gly Leu Ala Ala Leu Ser
            115                 120                 125
Asn Ala Asn Lys Pro Ser Ala Ser Pro Val Lys Val Leu Ser Asp Lys
        130                 135                 140
Ile Thr Gln Ile Tyr Ser Asp Val Lys Leu Pro Asn Ser Ala Ser Val
145                 150                 155                 160
Glu Gln Ile Gln Asn Lys Met Gln Glu Leu Asn Asp Leu Leu Glu Glu
                165                 170                 175
Leu Arg Glu Ser Phe Asp Gly Tyr Leu Gly Gly Asn Ala Phe Ala Asn
            180                 185                 190
Gln Ile Gln Leu Asn Phe Gln Ala Thr Ala Gln Glu Ala Val Ala Ala
        195                 200                 205
Ala Ala Val Arg Leu Leu Asn Gly Asn Asp Gln Ile Ala Gln Leu Tyr
    210                 215                 220
Lys Asp Leu Val Lys Leu Gln Arg His Ala Gly Ile Lys Lys Ala Met
225                 230                 235                 240
Glu Lys Leu Ala Ala Gln Ala Glu Phe Asp Leu Ser Met Ile Val
                245                 250                 255
Gly Gln Val Lys Leu Tyr Ala Asp Leu Phe Ile Thr Glu Ser Phe Ser
            260                 265                 270
```

<210> SEQ ID NO 3
<211> LENGTH: 272
<212> TYPE: PRT
<213> ORGANISM: Artificial Sequence
<220> FEATURE:
<223> OTHER INFORMATION: Karp_A

<400> SEQUENCE: 3

```
Ser Ala Ser Ala Ile Glu Leu Gly Asp Glu Gly Gly Leu Glu Cys Gly
1               5                   10                  15
Pro Tyr Ala Lys Val Gly Val Val Gly Gly Met Ile Thr Gly Val Glu
                20                  25                  30
Ser Thr Arg Leu Asp Pro Ala Asp Ala Asp Gly Lys Lys His Leu Pro
            35                  40                  45
Leu Thr Thr Ser Met Pro Phe Gly Gly Thr Leu Ala Ala Gly Met Thr
        50                  55                  60
Ile Ala Gln Gly Phe Arg Ala Glu Leu Gly Val Met Tyr Leu Thr Asn
65                  70                  75                  80
Ile Lys Leu Thr Pro Pro Gln Pro Thr Ile Met Pro Ile Ser Ile Ala
                85                  90                  95
Asp Arg Asp Phe Gly Ile Asp Arg Ile Ala Trp Leu Lys Asn Cys Ala
                100                 105                 110
Gly Ile Asp Tyr Trp Arg Tyr Leu Val Val Gly Leu Ala Ala Leu Ser
            115                 120                 125
Asn Ala Asn Lys Pro Ser Ala Ser Pro Val Lys Val Leu Ser Asp Lys
        130                 135                 140
Ile Thr Gln Ile Tyr Ser Asp Ile Lys Leu Pro Asn Ser Ala Ser Val
145                 150                 155                 160
Glu Gln Ile Gln Asn Lys Met Gln Glu Leu Asn Asp Val Leu Glu Glu
                165                 170                 175
Leu Arg Glu Ser Phe Asp Gly Tyr Leu Gly Gly Asn Ala Phe Ala Asn
```

```
                180                 185                 190
Gln Ile Gln Leu Asn Phe Gln Ala Thr Ala Gln Glu Ala Val Ala Ala
            195                 200                 205
Ala Ala Val Arg Leu Leu Asn Gly Asn Asp Gln Ile Glu Gln Leu Tyr
        210                 215                 220
Lys Asp Leu Val Lys Leu Gln Arg His Ala Gly Ile Lys Lys Ala Met
225                 230                 235                 240
Glu Lys Leu Ala Ala Gln Glu Ala Glu Phe Asp Leu Ser Met Ile Val
                245                 250                 255
Gly Gln Val Lys Leu Tyr Ala Asp Val Met Ile Thr Glu Ser Phe Ser
            260                 265                 270
```

<210> SEQ ID NO 4
<211> LENGTH: 272
<212> TYPE: PRT
<213> ORGANISM: Artificial Sequence
<220> FEATURE:
<223> OTHER INFORMATION: Saitama

<400> SEQUENCE: 4

```
Ser Ala Ser Ala Ile Glu Leu Gly Asp Glu Gly Gly Leu Glu Cys Gly
1               5                   10                  15
Pro Tyr Ala Lys Val Gly Val Gly Gly Met Ile Thr Gly Ala Glu
            20                  25                  30
Ser Ala Arg Leu Asp Gln Ala Asp Thr Thr Gly Lys Lys His Leu Pro
        35                  40                  45
Leu Thr Thr Ser Met Pro Phe Gly Gly Thr Leu Asn Ala Gly Ile Thr
    50                  55                  60
Ile Thr Pro Trp Leu Arg Ala Glu Leu Gly Val Met Tyr Leu Arg Asn
65                  70                  75                  80
Ile Lys Leu Thr Pro Pro Gln Pro Thr Ile Met Pro Ile Ser Ile Ala
                85                  90                  95
Asp Arg Asp Phe Ala Ile Asp Arg Val Ala Trp Leu Lys Asn Tyr Ala
            100                 105                 110
Gly Ile Asp Tyr Trp Arg Tyr Met Val Ile Gly Leu Ala Ala Leu Ser
        115                 120                 125
Asn Ala Asn Lys Pro Ser Asp Pro Val Lys Val Leu Ser Asp Lys
    130                 135                 140
Ile Thr Gln Ile Tyr Asn Asp Ile Arg Leu Pro Asn Ser Ala Ser Val
145                 150                 155                 160
Glu Gln Ile Gln Asn Lys Met Gln Glu Leu Asn Glu Leu Leu Glu Glu
                165                 170                 175
Val Arg Asp Ser Phe Glu Gly Tyr Ile Gly Gly Asn Ala Phe Ala Asn
            180                 185                 190
Gln Ile Gln Leu Asn Phe Gln Ala Thr Ala Gln Glu Ala Ala Ala Ala
            195                 200                 205
Ala Ala Val Arg Leu Leu Asn Gly Asn Asp Gln Ile Val Gln Leu Tyr
        210                 215                 220
Lys Asp Leu Val Lys Leu Lys Arg His Ala Gly Phe Lys Lys Ser Met
225                 230                 235                 240
Asp Lys Leu Ala Ala Gln Glu Thr Glu Phe Asp Leu Ser Met Ile Val
                245                 250                 255
Gly Gln Val Lys Leu Tyr Ala Asp Leu Val Ala Thr Glu Ser Phe Ser
            260                 265                 270
```

-continued

<210> SEQ ID NO 5
<211> LENGTH: 271
<212> TYPE: PRT
<213> ORGANISM: Artificial Sequence
<220> FEATURE:
<223> OTHER INFORMATION: Boryong

<400> SEQUENCE: 5

```
Ser Ala Ser Ala Ile Glu Leu Glu Asp Glu Val Gly Leu Glu Cys Gly
1               5                   10                  15

Pro Tyr Ala Lys Val Gly Val Val Gly Gly Met Ile Thr Gly Ala Glu
            20                  25                  30

Ser Thr Arg Leu Asp Ser Thr Asp Ser Glu Gly Lys Lys His Leu Ser
        35                  40                  45

Leu Thr Thr Gly Leu Pro Phe Gly Gly Thr Leu Ala Ala Gly Met Thr
    50                  55                  60

Ile Ala Pro Gly Phe Arg Ala Glu Leu Gly Val Met Tyr Leu Arg Asn
65                  70                  75                  80

Ile Lys Leu Thr Pro Pro Gln Pro Thr Met Met Pro Ile Ser Ile Ala
                85                  90                  95

Asp Arg Asp Phe Gly Ile Asp Arg Ile Ala Trp Leu Lys Asn Cys Ala
            100                 105                 110

Gly Ile Asp Tyr Trp Arg Ser Leu Val Val Gly Leu Ala Ala Leu Ser
        115                 120                 125

Asn Ala Asn Lys Pro Ser Ala Ser Pro Val Lys Val Leu Ser Asp Lys
    130                 135                 140

Ile Ile Gln Ile Tyr Ser Asp Ile Lys Leu Pro Asn Ser Ala Ser Ile
145                 150                 155                 160

Glu Gln Ile Gln Ser Lys Ile Gln Glu Leu Gly Asp Thr Leu Glu Glu
                165                 170                 175

Leu Arg Asp Ser Phe Asp Gly Tyr Ile Asn Asn Ala Phe Val Asn Gln
            180                 185                 190

Ile His Leu Asn Phe Gln Ala Thr Ala Gln Glu Ala Val Ala Ala Ala
        195                 200                 205

Ala Val Arg Leu Leu Asn Gly Ser Asp Gln Ile Ala Gln Leu Tyr Lys
    210                 215                 220

Asp Leu Val Lys Leu Gln Arg His Ala Gly Ile Arg Lys Ala Met Glu
225                 230                 235                 240

Lys Leu Ala Ala Gln Glu Thr Glu Phe Asp Leu Ser Met Val Val Gly
                245                 250                 255

Gln Val Lys Leu Tyr Ala Asp Leu Val Thr Thr Glu Ser Phe Ser
            260                 265                 270
```

<210> SEQ ID NO 6
<211> LENGTH: 271
<212> TYPE: PRT
<213> ORGANISM: Artificial Sequence
<220> FEATURE:
<223> OTHER INFORMATION: JG_C

<400> SEQUENCE: 6

```
Ser Ala Ser Ala Ile Glu Leu Gly Asp Glu Gly Gly Leu Glu Cys Gly
1               5                   10                  15

Pro Tyr Ala Lys Val Gly Val Val Gly Gly Met Ile Thr Gly Val Glu
            20                  25                  30

Ser Thr Arg Leu Asp Pro Ala Asp Ala Asp Gly Lys Lys His Leu Pro
        35                  40                  45
```

Leu Thr Thr Ser Met Pro Phe Gly Gly Thr Leu Ala Ala Gly Met Thr
         50                  55                  60

Ile Ala Pro Gly Phe Arg Ala Glu Leu Gly Val Met Tyr Leu Arg Asn
 65                  70                  75                  80

Ile Lys Leu Thr Pro Pro Gln Pro Thr Ile Met Pro Ile Ser Ile Ala
                 85                  90                  95

Asp Arg Asp Glu Gly Val Asp Arg Ile Ala Trp Leu Lys Asn Tyr Ala
                100                 105                 110

Gly Ile Asp Tyr Trp Arg His Leu Val Val Gly Val Thr Ala Leu Ser
                115                 120                 125

His Ala Asn Lys Pro Ser Val Thr Pro Val Lys Val Leu Ser Asp Lys
        130                 135                 140

Ile Thr Lys Ile Tyr Ser Asp Ile Arg Leu Pro Asn Ser Ala Ser Val
145                 150                 155                 160

Glu Gln Ile Gln Ala Lys Met Glu Leu Asn Asn Ile Leu Glu Glu
                165                 170                 175

Leu Arg Glu Ser Phe Asp Gly Tyr Leu Ala Asn Ala Phe Ala Asn Gln
                180                 185                 190

Ile Gln Leu Asn Phe Gln Val Thr Ala Gln Asp Ala Ala Ala Ala
        195                 200                 205

Ala Val Arg Ala Leu Asn Gly Asn Glu Gln Ile Ile Gln Leu Tyr Lys
        210                 215                 220

Asp Leu Val Lys Leu Gln Arg His Ala Gly Ile Arg Lys Ala Met Glu
225                 230                 235                 240

Gln Leu Ala Val Gln Glu Thr Glu Phe Asp Leu Ser Met Ile Val Gly
                245                 250                 255

Gln Val Lys Leu Tyr Ala Asp Leu Phe Thr Thr Glu Ser Phe Ser
                260                 265                 270

<210> SEQ ID NO 7
<211> LENGTH: 271
<212> TYPE: PRT
<213> ORGANISM: Artificial Sequence
<220> FEATURE:
<223> OTHER INFORMATION: Kawasaki

<400> SEQUENCE: 7

Ser Ala Ser Ala Ile Glu Leu Gly Asp Glu Gly Val Leu Glu Cys Gly
 1               5                  10                  15

Pro Tyr Ala Lys Ile Gly Val Val Gly Gly Met Val Thr Gly Val Glu
                 20                  25                  30

Ser Ala Arg Leu Asp Pro Ala Asp Val Asp Cys Lys Lys His Leu Ser
            35                  40                  45

Leu Thr Thr Met Leu Pro Phe Gly Gly Thr Leu Ala Ala Gly Met Thr
         50                  55                  60

Ile Ala Pro Gly Phe Arg Ala Glu Leu Gly Val Met Tyr Leu Arg Asn
 65                  70                  75                  80

Ile Lys Leu Thr Pro Pro Gln Pro Thr Ile Met Pro Ile Ser Ile Ala
                 85                  90                  95

Asp Arg Asp Leu Gly Val Asp Arg Ile Ala Trp Leu Lys Asn Tyr Ala
                100                 105                 110

Gly Ile Asp Tyr Trp Arg Tyr Leu Val Val Gly Val Thr Ala Leu Ser
                115                 120                 125

Asn Ala Asn Lys Pro Ser Val Ser Ser Val Lys Val Leu Ser Asp Lys
        130                 135                 140

```
Ile Thr Gln Ile Tyr Ser Asp Ile Arg Leu Pro Asn Ser Ala Ser Val
145                 150                 155                 160

Glu Gln Ile Gln Thr Lys Met Gln Glu Leu Asn Asp Val Leu Glu Glu
            165                 170                 175

Leu Arg Glu Ser Phe Asp Gly Tyr Leu Ala Asn Ala Phe Ala Asn Gln
            180                 185                 190

Ile Gln Leu Asn Phe Gln Val Thr Ala Gln Glu Ala Ala Ala Ala Ala
            195                 200                 205

Ala Val Arg Ala Leu Asn Gly Asn Glu Gln Ile Ile Gln Leu Tyr Lys
            210                 215                 220

Asp Leu Val Lys Leu Gln Arg His Ala Gly Ile Arg Lys Ala Met Glu
225                 230                 235                 240

Lys Leu Ala Ala Gln Glu Val Glu Leu Asp Leu Ser Met Ile Val Ala
            245                 250                 255

Gln Val Lys Leu Tyr Ala Asp Val Val Ala Thr Glu Ser Phe Ser
            260                 265                 270

<210> SEQ ID NO 8
<211> LENGTH: 273
<212> TYPE: PRT
<213> ORGANISM: Artificial Sequence
<220> FEATURE:
<223> OTHER INFORMATION: JG_B

<400> SEQUENCE: 8

Ser Ala Ser Ala Met Glu Phe Gly Asp Glu Gly Gly Gly Gly Leu Glu
1               5                   10                  15

Cys Gly Pro Tyr Ala Lys Val Gly Val Val Gly Gly Met Ile Thr Gly
            20                  25                  30

Val Glu Ser Thr Arg Leu Asp Ser Ala Asp Ala Gly Gly Lys Arg Tyr
            35                  40                  45

Leu Pro Leu Thr Thr Gly Leu Pro Phe Gly Gly Thr Leu Ala Ala Gly
            50                  55                  60

Met Thr Ile Ala Pro Gly Phe Arg Ala Glu Leu Gly Val Met Tyr Leu
65                  70                  75                  80

Arg Asn Ile Lys Leu Val Pro Pro Gln Pro Thr Ile Met Pro Ile Ser
            85                  90                  95

Ile Ala Asp Arg Asp Val Gly Val Asp Arg Ile Ala Trp Leu Lys Asn
            100                 105                 110

Tyr Ala Gly Ile Asp Tyr Trp Arg His Leu Val Val Gly Val Thr Ala
            115                 120                 125

Leu Ser His Ala Asn Lys Pro Ser Val Thr Pro Val Lys Val Leu Ser
            130                 135                 140

Asp Lys Ile Thr Lys Ile Tyr Ser Asp Ile Arg Leu Pro Asn Ser Ala
145                 150                 155                 160

Ser Val Glu Gln Ile Gln Ala Lys Met Gln Glu Leu Asn Asn Val Leu
            165                 170                 175

Glu Glu Leu Arg Glu Ser Phe Glu Gly Tyr Leu Ala Asn Ala Phe Ala
            180                 185                 190

Asn Gln Ile Gln Leu Asn Phe Gln Val Thr Ala Gln Glu Ala Ala Ala
            195                 200                 205

Ala Ala Ala Val Arg Ala Leu Asn Gly Asn Glu Gln Ile Ile Gln Leu
            210                 215                 220

Tyr Lys Asp Leu Val Lys Leu Gln Arg His Ala Gly Ile Ser Lys Ala
225                 230                 235                 240
```

```
Met Glu Gln Leu Ala Ala Gln Glu Thr Glu Phe Asp Leu Ser Met Val
            245                 250                 255

Val Gly Gln Val Lys Leu Tyr Ala Asp Leu Val Ala Thr Glu Ser Phe
        260                 265                 270

Ser

<210> SEQ ID NO 9
<211> LENGTH: 271
<212> TYPE: PRT
<213> ORGANISM: Artificial Sequence
<220> FEATURE:
<223> OTHER INFORMATION: JG_A

<400> SEQUENCE: 9

Leu Ala Ser Ala Ile Glu Leu Gly Asp Glu Gly Gly Leu Glu Cys Gly
1               5                   10                  15

Pro Tyr Ala Lys Val Gly Val Gly Gly Met Ile Thr Gly Val Glu
            20                  25                  30

Ser Thr Arg Leu Asp Ser Ala Asp Ala Asp Gly Lys Lys His Leu Ser
        35                  40                  45

Leu Ile Thr Gly Ile Pro Phe Gly Gly Thr Leu Ala Ala Gly Met Thr
50                  55                  60

Ile Ala Pro Gly Phe Arg Ala Glu Leu Gly Val Met Tyr Leu Arg Asn
65                  70                  75                  80

Ile Lys Leu Thr Pro Pro Gln Pro Thr Ile Met Pro Ile Ser Ile Ala
                85                  90                  95

Asp Arg Asp Val Gly Val Asp Arg Ile Ala Trp Leu Lys Asp Tyr Ala
            100                 105                 110

Gly Ile Asp Tyr Trp Arg His Leu Val Val Gly Val Thr Ala Leu Ser
        115                 120                 125

His Ala Asn Lys Pro Ser Val Thr Pro Val Lys Val Leu Ser Asp Lys
130                 135                 140

Ile Thr Lys Ile Tyr Ser Asp Ile Arg Leu Pro Asn Ser Ala Ser Val
145                 150                 155                 160

Glu Gln Ile Gln Ala Lys Met Gln Glu Leu Asn Asn Val Leu Glu Glu
                165                 170                 175

Leu Arg Glu Ser Phe Asp Gly Tyr Leu Ala Asn Ala Phe Val Asn Gln
            180                 185                 190

Ile Gln Leu Asn Phe Gln Val Thr Ala Gln Glu Ala Ala Ala Ala Ala
        195                 200                 205

Ala Val Arg Ala Leu Asn Gly Asn Glu Gln Ile Ile Gln Leu Tyr Lys
210                 215                 220

Asp Leu Val Lys Leu Gln Arg His Ala Gly Ile Arg Lys Ala Met Glu
225                 230                 235                 240

Gln Leu Ala Ala Gln Glu Thr Glu Phe Asp Leu Ser Met Ile Val Gly
                245                 250                 255

Gln Val Lys Leu Tyr Ala Asp Leu Phe Thr Thr Glu Ser Phe Ser
            260                 265                 270

<210> SEQ ID NO 10
<211> LENGTH: 271
<212> TYPE: PRT
<213> ORGANISM: Artificial Sequence
<220> FEATURE:
<223> OTHER INFORMATION: Gilliam

<400> SEQUENCE: 10
```

```
Ser Ala Ser Ala Ile Glu Leu Gly Glu Gly Gly Leu Glu Cys Gly
1               5                   10                  15

Pro Tyr Gly Lys Val Gly Ile Val Gly Gly Met Ile Thr Gly Ala Glu
            20                  25                  30

Ser Thr Arg Leu Asp Ser Thr Asp Ser Glu Gly Lys Lys His Leu Ser
            35                  40                  45

Leu Thr Thr Gly Leu Pro Phe Gly Gly Thr Leu Ala Ala Gly Met Thr
50                      55                  60

Ile Ala Pro Gly Phe Arg Ala Glu Leu Gly Val Met Tyr Leu Arg Asn
65                  70                  75                  80

Ile Lys Leu Thr Pro Pro Gln Pro Thr Ile Met Pro Ile Ser Ile Ala
                85                  90                  95

Asp Arg Asp Val Gly Val Asp Arg Ile Ala Trp Leu Lys Asn Tyr Ala
                100                 105                 110

Gly Ile Asp Tyr Trp Arg His Leu Val Val Gly Val Thr Ala Leu Ser
                115                 120                 125

His Ala Asn Lys Pro Ser Val Thr Pro Val Lys Val Leu Ser Asp Lys
                130                 135                 140

Ile Thr Lys Ile Tyr Ser Asp Ile Lys Leu Pro Asn Ser Ala Ser Val
145                 150                 155                 160

Glu Gln Ile Gln Ser Lys Met Gln Glu Leu Asn Asp Val Leu Glu Asp
                165                 170                 175

Leu Arg Asp Ser Phe Asp Gly Tyr Met Gly Asn Ala Phe Ala Asn Gln
                180                 185                 190

Ile Gln Leu Asn Phe Gln Ala Thr Ala Gln Glu Ala Val Ala Ala Ala
                195                 200                 205

Ala Val Arg Leu Leu Asn Gly Asn Asp Gln Ile Ala Gln Leu Tyr Lys
                210                 215                 220

Asp Leu Val Lys Leu Gln Arg His Ala Gly Val Lys Lys Ala Met Glu
225                 230                 235                 240

Lys Leu Ala Ala Gln Glu Thr Glu Phe Asp Leu Ser Met Ile Val Gly
                245                 250                 255

Gln Val Lys Leu Tyr Ala Asp Leu Phe Thr Thr Glu Ser Phe Ser
                260                 265                 270

<210> SEQ ID NO 11
<211> LENGTH: 271
<212> TYPE: PRT
<213> ORGANISM: Artificial Sequence
<220> FEATURE:
<223> OTHER INFORMATION: TD

<400> SEQUENCE: 11

Ser Ala Ser Ala Ile Glu Leu Gly Asp Glu Gly Gly Leu Glu Cys Gly
1               5                   10                  15

Pro Tyr Ala Lys Val Gly Val Val Gly Gly Ile Ile Thr Gly Val Glu
            20                  25                  30

Ser Ala Arg Leu Asp Pro Ala Asp Thr Asn Gly Lys Lys Leu Leu Pro
            35                  40                  45

Leu Thr Thr Ser Met Pro Phe Gly Gly Thr Leu Ala Ala Gly Met Thr
50                      55                  60

Ile Ala Gln Gly Phe Arg Ala Glu Leu Gly Val Met Tyr Leu Arg Asn
65                  70                  75                  80

Ile Lys Ile Thr Pro Pro Gln Pro Thr Ile Met Ser Ile Ser Ile Ala
                85                  90                  95
```

```
Asp Arg Asn Ala Gly Val Asp Arg Ile Ala Trp Leu Arg Asn Tyr Ala
            100                 105                 110

Gly Ile Glu Tyr Trp Arg His Leu Val Val Gly Val Ala Ala Met Ser
        115                 120                 125

Asn Ala Asn Lys Pro Ser Thr Ser Ala Val Lys Val Leu Gly Asp Lys
    130                 135                 140

Ile Ser Gln Ile Tyr Cys Asp Ile Lys Leu Pro Asn Ser Ala Ser Val
145                 150                 155                 160

Glu Gln Ile Gln Gly Lys Met Gln Glu Leu Gly Asp Ile Leu Glu Ala
                165                 170                 175

Leu Arg Asp Ser Phe Glu Gly Tyr Ile Ala Asn Ala Phe Ala Asn Gln
        180                 185                 190

Ile Gln Leu Asn Phe Gln Val Thr Ala Gln Glu Ala Val Ala Ala Ala
    195                 200                 205

Ala Val Arg Ala Leu Asn Arg Asn Glu Gln Ile Ala Gln Leu Tyr Lys
210                 215                 220

Asp Leu Val Lys Leu Gln Arg His Ala Gly Ile Arg Lys Ala Met Glu
225                 230                 235                 240

Lys Leu Ala Ala Gln Glu Thr Glu Phe Asp Leu Ser Met Ile Val Gly
                245                 250                 255

Gln Val Lys Leu Tyr Ala Asp Leu Met Thr Thr Glu Ser Phe Ser
        260                 265                 270

<210> SEQ ID NO 12
<211> LENGTH: 271
<212> TYPE: PRT
<213> ORGANISM: Artificial Sequence
<220> FEATURE:
<223> OTHER INFORMATION: TA763_B

<400> SEQUENCE: 12

Ser Ala Ser Ala Ile Glu Leu Gly Asp Glu Gly Gly Leu Glu Cys Gly
1               5                   10                  15

Pro Tyr Ala Lys Val Gly Ile Val Gly Met Ile Thr Gly Ala Glu
            20                  25                  30

Ser Thr Arg Leu Asp Ser Ser Asp Ala Glu Gly Lys Lys Arg Leu Ser
        35                  40                  45

Leu Thr Thr Ser Val Pro Phe Gly Gly Thr Leu Ala Ala Gly Ile Thr
    50                  55                  60

Ile Ala Gln Gly Phe Arg Ala Glu Leu Gly Val Met Tyr Leu Thr Asn
65                  70                  75                  80

Ile Lys Leu Thr Pro Pro Gln Pro Val Ile Met Pro Ile Ser Thr Ala
                85                  90                  95

Asp Arg Asp Met Gly Val Asp Arg Ile Ala Trp Leu Lys Gln Tyr Ala
            100                 105                 110

Gly Ile Asp Tyr Trp Arg His Leu Val Val Gly Ile Ala Ala Leu Ser
        115                 120                 125

Asn Ala Asn Lys Pro Ser Ala Ser Pro Val Lys Val Leu Ser Asp Lys
    130                 135                 140

Ile Thr Lys Ile Tyr Ser Asp Ile Lys Leu Pro Asn Ser Ala Ser Ile
145                 150                 155                 160

Glu Gln Ile Gln Arg Lys Met Gln Glu Leu Asn Asp Val Leu Glu Gly
                165                 170                 175

Leu Arg Asp Ala Phe Asp Gly Tyr Ile Asn Asn Ala Phe Val Asp Gln
        180                 185                 190
```

Ile Gln Leu Asn Phe Gln Ala Thr Ala Gln Glu Ala Val Ala Ala Ala
            195                 200                 205

Ala Val Arg Leu Leu Asn Gly Asn Asp Gln Ile Val Gln Leu Tyr Lys
        210                 215                 220

Asp Leu Val Lys Leu Gln Arg His Ala Gly Ile Lys Lys Ala Met Glu
225                 230                 235                 240

Lys Leu Ala Ala Gln Glu Ala Glu Phe Asp Leu Ser Met Ile Val Gly
                245                 250                 255

Gln Val Lys Leu Tyr Ala Asp Leu Met Thr Thr Glu Ser Phe Ser
            260                 265                 270

<210> SEQ ID NO 13
<211> LENGTH: 271
<212> TYPE: PRT
<213> ORGANISM: Artificial Sequence
<220> FEATURE:
<223> OTHER INFORMATION: TA763_A

<400> SEQUENCE: 13

Ser Ala Ser Ala Ile Glu Leu Gly Asp Glu Gly Gly Leu Glu Cys Gly
1               5                   10                  15

Pro Tyr Ala Lys Val Gly Val Val Gly Gly Met Ile Thr Gly Val Glu
            20                  25                  30

Ser Ala Arg Leu Asp Pro Ala Asp His Glu Gly Lys Lys His Leu Pro
        35                  40                  45

Leu Thr Thr Ser Met Pro Phe Gly Gly Thr Leu Ala Ala Gly Met Thr
    50                  55                  60

Ile Ala Gln Gly Phe Arg Ala Glu Leu Gly Val Met Tyr Leu Arg Asn
65                  70                  75                  80

Ile Lys Leu Thr Pro Pro Gln Pro Thr Ile Met Pro Ile Ser Ile Ala
                85                  90                  95

Asp Arg Asp Phe Gly Val Asp Arg Ile Ala Trp Leu Lys Glu Tyr Ala
            100                 105                 110

Gly Ile Asp Tyr Trp Arg His Leu Val Val Gly Val Thr Ala Leu Ser
        115                 120                 125

Asn Ala Asn Lys Pro Ser Ala Ser Pro Val Lys Ile Leu Ser Glu Lys
    130                 135                 140

Ile Thr Gln Ile Tyr Ser Asp Ile Arg Leu Pro Asn Ser Ala Ser Val
145                 150                 155                 160

Glu Gln Ile Gln Ser Lys Met Gln Glu Leu Ser Asp Leu Leu Glu Glu
                165                 170                 175

Leu Arg Asp Ser Phe Asp Gly Tyr Ile Ser Asn Ala Phe Ala Gly Gln
            180                 185                 190

Ile Gln Leu Asn Phe Gln Ala Thr Ala Gln Glu Ala Val Ala Ala Ala
        195                 200                 205

Ala Val Arg Leu Leu Asn Gly Asn Asp Gln Ile Ala Gln Leu Tyr Lys
    210                 215                 220

Asp Leu Val Lys Leu Gln Arg His Ala Gly Ile Arg Lys Ala Met Glu
225                 230                 235                 240

Lys Leu Ala Ala Gln Glu Thr Glu Phe Asp Leu Ser Met Ile Val Gly
                245                 250                 255

Gln Val Lys Leu Tyr Ala Asp Leu Met Thr Thr Glu Ser Phe Ser
            260                 265                 270

<210> SEQ ID NO 14
<211> LENGTH: 272

```
<212> TYPE: PRT
<213> ORGANISM: Artificial Sequence
<220> FEATURE:
<223> OTHER INFORMATION: Kato_B

<400> SEQUENCE: 14

Ser Ala Ser Ala Ile Glu Leu Gly Asp Glu Gly Gly Leu Glu Cys Gly
1               5                   10                  15

Pro Tyr Ala Lys Val Gly Val Gly Gly Met Ile Thr Gly Val Glu
            20                  25                  30

Ser Thr Arg Leu Asp Pro Ala Asp Ala Gly Gly Lys Lys His Leu Pro
        35                  40                  45

Leu Thr Thr Gly Leu Pro Phe Gly Gly Thr Leu Ala Ala Gly Met Thr
    50                  55                  60

Ile Ala Pro Gly Phe Arg Ala Glu Leu Gly Val Met Tyr Leu Thr Asn
65                  70                  75                  80

Val Lys Leu Thr Pro Pro Gln Pro Thr Ile Met Pro Ile Ser Ile Ala
                85                  90                  95

Asp Arg Asp Leu Gly Val Asp Arg Ile Ala Trp Leu Lys Asn Tyr Ala
            100                 105                 110

Gly Ile Asp Tyr Trp Arg His Ile Val Gly Val Thr Ala Met Ser
            115                 120                 125

Asn Ala Asn Lys Pro Ser Val Ser Pro Val Lys Val Leu Ser Asp Lys
130                 135                 140

Ile Val Gln Ile Tyr Arg Asp Val Lys Leu Pro Asn Ser Ala Ser Val
145                 150                 155                 160

Glu Gln Ile Gln Asn Lys Met Gln Glu Leu Asn Asp Ile Leu Asp Asp
                165                 170                 175

Ile Arg Asp Ser Phe Asp Gly Cys Ile Gly Gly Asn Ala Phe Ala Asn
            180                 185                 190

Gln Ile Gln Leu Asn Phe Gln Ala Thr Ala Gln Glu Ala Ala Ala
            195                 200                 205

Ala Ala Val Arg Val Leu Asn Asn Asn Asp Gln Ile Ile Gln Leu Tyr
        210                 215                 220

Lys Asp Leu Val Lys Leu Lys Arg His Ala Gly Ile Lys Lys Ala Met
225                 230                 235                 240

Glu Glu Leu Ala Ala Gln Glu Thr Glu Phe Asp Leu Ser Met Ile Val
                245                 250                 255

Gly Gln Val Lys Leu Tyr Ala Asp Leu Phe Thr Thr Glu Ser Phe Ser
            260                 265                 270

<210> SEQ ID NO 15
<211> LENGTH: 271
<212> TYPE: PRT
<213> ORGANISM: Artificial Sequence
<220> FEATURE:
<223> OTHER INFORMATION: Kato_A

<400> SEQUENCE: 15

Ser Ala Ser Ala Ile Glu Leu Gly Glu Gly Gly Leu Glu Cys Gly
1               5                   10                  15

Pro Tyr Ala Lys Val Gly Val Val Gly Met Ile Thr Gly Val Glu
            20                  25                  30

Ser Thr Arg Leu Asp Pro Ala Asp Val Asp Gly Lys Lys His Leu Pro
        35                  40                  45

Leu Thr Thr Gly Leu Pro Phe Gly Gly Thr Leu Ala Ala Gly Met Thr
    50                  55                  60
```

```
Ile Ala Pro Gly Phe Arg Ala Glu Leu Gly Val Met Tyr Leu Thr Asn
 65                  70                  75                  80

Ile Lys Leu Thr Pro Pro Gln Pro Thr Ile Met Pro Ile Ser Ile Ala
                 85                  90                  95

Asp Arg Asp Phe Gly Val Asp Arg Ile Ala Trp Leu Lys Glu Tyr Ala
            100                 105                 110

Gly Ile Asp Tyr Trp Arg Asp Met Val Val Gly Ile Thr Ala Met Ser
        115                 120                 125

Asn Ala Asn Lys Pro Ser Ala Ser Pro Ile Lys Val Leu Ser Asp Lys
    130                 135                 140

Ile Ser Gln Ile Tyr Asp Asp Ile Arg Leu Pro Asn Ser Ala Ser Val
145                 150                 155                 160

Glu Gln Ile Gln Ser Lys Met Gln Glu Leu Ser Glu Thr Leu Glu Glu
                165                 170                 175

Leu Arg Glu Ser Phe Asp Gly Cys Ile Gly Asn Ala Phe Ala Asn Gln
            180                 185                 190

Ile Gln Leu Asp Phe Gln Ala Thr Val Gln Glu Ala Thr Ala Ala Ala
        195                 200                 205

Ala Val Arg Val Leu Asn Gly Asn Gly Gln Ile Ile Gln Leu Tyr Lys
    210                 215                 220

Asp Leu Val Lys Leu Lys Arg His Ala Gly Ile Lys Lys Ala Met Glu
225                 230                 235                 240

Lys Leu Ala Ala Gln Glu Thr Glu Phe Asp Leu Ser Met Ile Val Gly
                245                 250                 255

Gln Val Lys Leu Tyr Ala Asp Leu Met Thr Thr Glu Ser Phe Ser
            260                 265                 270

<210> SEQ ID NO 16
<211> LENGTH: 272
<212> TYPE: PRT
<213> ORGANISM: Artificial Sequence
<220> FEATURE:
<223> OTHER INFORMATION: Shimokoshi

<400> SEQUENCE: 16

Ser Ala Asn Ala Ile Glu Phe Asp Glu Asn Ser Leu Glu Cys Gly Pro
  1               5                  10                  15

Tyr Ala Lys Val Gly Ile Val Gly Gly Val Leu Ser Gly Val Glu Ser
                 20                  25                  30

Ala Arg Leu Asp Pro Ala Asp Ser Glu Gly Lys Lys His Leu Pro Leu
             35                  40                  45

Ile Lys Gly Met Pro Phe Gly Val Thr Leu Ala Ala Gly Met Thr Ile
         50                  55                  60

Thr Pro Gly Val Arg Ala Glu Ile Ser Ala Met Tyr Leu Met Asn Val
 65                  70                  75                  80

Lys Leu Thr Pro Pro Gln Pro Asn Ile Met Pro Ile Ser Ile Ala Asp
                 85                  90                  95

Arg Asp Ile Ala Val Asp Arg Ile Ala Trp Leu Lys Asn Tyr Ala Gly
            100                 105                 110

Ile Asp Tyr Trp Arg Asp Val Val Val Gly Ile Thr Ala Leu Ser Asn
        115                 120                 125

Ala Asn Lys Pro Asn Val Ser Ala Val Lys Ile Leu Ser Asp Lys Ile
    130                 135                 140

Ser Gln Ile Tyr Ala Asp Ile Lys Leu Pro Asp Ser Ala Ser Val Asp
145                 150                 155                 160
```

Gln Ile Gln Asn Lys Val Gln Glu Leu Asn Lys Val Leu Glu Asp Val
                165                 170                 175

Arg Glu Ser Phe Asp Gly Phe Ile Leu Asn Ala Phe Ala Gln Pro Val
            180                 185                 190

Arg Leu Asn Phe Ala Ala Thr Ala Gln Glu Ala Ala Ala Ala Ala Ala
        195                 200                 205

Ile Arg Ala Leu Asn Asp Gly Glu Asn Asn Gly Ile Ile Gln Leu Tyr
    210                 215                 220

Lys Asp Leu Tyr Lys Leu Gln Arg Asn Val Ala Leu Lys Lys Ser Met
225                 230                 235                 240

Lys Gln Leu Gly Asp Glu Glu Ile Glu Phe Asp Leu His Met Ala Val
            245                 250                 255

Gly Gln Val Lys Leu Tyr Ala Asp Leu Phe Thr Ile Asp Ser Phe Ser
        260                 265                 270

<210> SEQ ID NO 17
<211> LENGTH: 271
<212> TYPE: PRT
<213> ORGANISM: Artificial Sequence
<220> FEATURE:
<223> OTHER INFORMATION: TA686

<400> SEQUENCE: 17

Ser Ala Ser Ala Ile Glu Leu Gly Asp Glu Gly Gly Leu Glu Cys Gly
1               5                   10                  15

Pro Tyr Ala Arg Val Gly Val Val Gly Gly Met Ile Thr Gly Val Glu
            20                  25                  30

Ser Thr Arg Leu Asp Ser Thr Asp Pro Glu Gly Lys Lys His Leu Ser
        35                  40                  45

Leu Thr Thr Gly Leu Pro Phe Gly Gly Thr Leu Ala Ala Gly Met Thr
    50                  55                  60

Ile Ala Pro Gly Phe Arg Ala Glu Leu Gly Val Met Tyr Leu Arg Asn
65                  70                  75                  80

Ile Lys Leu Thr Pro Pro Ala Ile Val Met Pro Ile Ser Ile Ala
            85                  90                  95

Asp Arg Asp Leu Gly Val Asp Arg Ile Ala Trp Leu Lys Glu Tyr Ala
            100                 105                 110

Gly Ile Asp Tyr Trp Arg His Leu Val Val Gly Ile Ala Ala Leu Ser
        115                 120                 125

Asn Ala Asn Lys Pro Asn Ala Ser Pro Val Lys Val Leu Ser Asp Lys
    130                 135                 140

Ile Ser Gln Ile Tyr Lys Asp Ile Lys Leu Ala Asn Ser Ala Ser Val
145                 150                 155                 160

Glu Gln Ile Gln Ser Lys Met Gln Glu Leu Asn Asp Ile Leu Glu Asp
            165                 170                 175

Leu Arg Glu Ser Phe Asp Gly Tyr Ile Ser Asn Ala Phe Ala Asn Gln
            180                 185                 190

Ile Gln Leu Asp Phe His Ala Thr Ala Gln Glu Ala Ala Ala Ala Ala
        195                 200                 205

Ala Val Arg Val Leu Asn Asn Glu Gln Ile Ile Gln Leu Tyr Lys
    210                 215                 220

Asp Leu Val Lys Leu Lys Arg His Ala Gly Ile Arg Lys Ala Met Glu
225                 230                 235                 240

Gln Leu Ala Ala Gln Glu Thr Glu Phe Asp Leu Ser Met Ile Val Gly
            245                 250                 255

```
Gln Val Lys Leu Tyr Ala Asp Val Phe Thr Thr Glu Ser Phe Ser
        260                 265                 270
```

<210> SEQ ID NO 18
<211> LENGTH: 272
<212> TYPE: PRT
<213> ORGANISM: Artificial Sequence
<220> FEATURE:
<223> OTHER INFORMATION: Karp

<400> SEQUENCE: 18

```
Ser Ala Ser Ala Ile Glu Leu Gly Asp Glu Gly Gly Leu Glu Cys Gly
1               5                   10                  15

Pro Tyr Ala Lys Val Gly Val Gly Gly Met Ile Thr Gly Val Glu
            20                  25                  30

Ser Thr Arg Leu Asp Ser Ala Asp Ala Asp Gly Lys Lys His Leu Pro
        35                  40                  45

Leu Thr Thr Ser Met Pro Phe Gly Gly Thr Leu Ala Ala Gly Met Thr
    50                  55                  60

Ile Ala Pro Gly Phe Arg Ala Glu Leu Gly Val Met Tyr Leu Thr Asn
65                  70                  75                  80

Ile Lys Leu Thr Pro Pro Gln Pro Thr Ile Met Pro Ile Ser Ile Ala
                85                  90                  95

Asp Arg Asp Phe Gly Ile Asp Arg Ile Ala Trp Leu Lys Asn Cys Ala
            100                 105                 110

Gly Ile Asp Tyr Trp Arg His Leu Val Val Gly Leu Ala Ala Leu Ser
        115                 120                 125

Asn Ala Asn Lys Pro Ser Ala Ser Pro Val Lys Val Leu Ser Asp Lys
    130                 135                 140

Ile Thr Gln Ile Tyr Ser Asp Ile Lys Leu Pro Asn Ser Ala Ser Val
145                 150                 155                 160

Glu Gln Ile Gln Asn Lys Met Gln Glu Leu Asn Asp Val Leu Glu Glu
                165                 170                 175

Leu Arg Asp Ser Phe Asp Gly Tyr Ile Gly Gly Asn Ala Phe Ala Asn
            180                 185                 190

Gln Ile Gln Leu Asn Phe Gln Ala Thr Ala Gln Glu Ala Val Ala Ala
        195                 200                 205

Ala Ala Val Arg Leu Leu Asn Gly Asn Asp Gln Ile Ala Gln Leu Tyr
    210                 215                 220

Lys Asp Leu Val Lys Leu Gln Arg His Ala Gly Ile Lys Lys Ala Met
225                 230                 235                 240

Glu Lys Leu Ala Ala Gln Glu Ala Glu Phe Asp Leu Ser Met Ile Val
                245                 250                 255

Gly Gln Val Lys Leu Tyr Ala Asp Leu Val Ile Thr Glu Ser Phe Ser
            260                 265                 270
```

<210> SEQ ID NO 19
<211> LENGTH: 271
<212> TYPE: PRT
<213> ORGANISM: Artificial Sequence
<220> FEATURE:
<223> OTHER INFORMATION: Gilliam

<400> SEQUENCE: 19

```
Ser Ala Ser Ala Ile Glu Leu Gly Asp Glu Gly Gly Leu Glu Cys Gly
1               5                   10                  15

Pro Tyr Ala Lys Val Gly Val Gly Gly Met Ile Thr Gly Val Glu
```

```
            20                  25                  30
Ser Thr Arg Leu Asp Ser Ala Asp Ala Asp Gly Lys Lys His Leu Ser
        35                  40                  45
Leu Thr Thr Gly Leu Pro Phe Gly Gly Thr Leu Ala Ala Gly Met Thr
    50                  55                  60
Ile Ala Pro Gly Phe Arg Ala Glu Leu Gly Val Met Tyr Leu Arg Asn
65                  70                  75                  80
Ile Lys Leu Thr Pro Pro Gln Pro Thr Ile Met Pro Ile Ser Ile Ala
                85                  90                  95
Asp Arg Asp Val Gly Val Asp Arg Ile Ala Trp Leu Lys Asn Tyr Ala
            100                 105                 110
Gly Ile Asp Tyr Trp Arg His Leu Val Val Gly Val Thr Ala Leu Ser
            115                 120                 125
His Ala Asn Lys Pro Ser Val Thr Pro Val Lys Val Leu Ser Asp Lys
        130                 135                 140
Ile Thr Lys Ile Tyr Ser Asp Ile Arg Leu Pro Asn Ser Ala Ser Val
145                 150                 155                 160
Glu Gln Ile Gln Ala Lys Met Gln Glu Leu Asn Asp Val Leu Glu Glu
                165                 170                 175
Leu Arg Glu Ser Phe Asp Gly Tyr Leu Ala Asn Ala Phe Ala Asn Gln
            180                 185                 190
Ile Gln Leu Asn Phe Gln Val Thr Ala Gln Glu Ala Ala Ala Ala Ala
        195                 200                 205
Ala Val Arg Ala Leu Asn Gly Asn Glu Gln Ile Ile Gln Leu Tyr Lys
    210                 215                 220
Asp Leu Val Lys Leu Gln Arg His Ala Gly Ile Arg Lys Ala Met Glu
225                 230                 235                 240
Gln Leu Ala Ala Gln Glu Thr Glu Phe Asp Leu Ser Met Ile Val Gly
                245                 250                 255
Gln Val Lys Leu Tyr Ala Asp Leu Phe Thr Thr Glu Ser Phe Ser
            260                 265                 270

<210> SEQ ID NO 20
<211> LENGTH: 271
<212> TYPE: PRT
<213> ORGANISM: Artificial Sequence
<220> FEATURE:
<223> OTHER INFORMATION: TA763

<400> SEQUENCE: 20

Ser Ala Ser Ala Ile Glu Leu Gly Asp Glu Gly Gly Leu Glu Cys Gly
1               5                   10                  15
Pro Tyr Ala Lys Val Gly Val Val Gly Gly Met Ile Thr Gly Val Glu
            20                  25                  30
Ser Thr Arg Leu Asp Ser Ala Asp Ala Glu Gly Lys Lys His Leu Pro
        35                  40                  45
Leu Thr Thr Ser Met Pro Phe Gly Gly Thr Leu Ala Ala Gly Met Thr
    50                  55                  60
Ile Ala Gln Gly Phe Arg Ala Glu Leu Gly Val Met Tyr Leu Thr Asn
65                  70                  75                  80
Ile Lys Leu Thr Pro Pro Gln Pro Val Ile Met Pro Ile Ser Thr Ala
                85                  90                  95
Asp Arg Asp Met Gly Val Asp Arg Ile Ala Trp Leu Lys Gln Tyr Ala
            100                 105                 110
Gly Ile Asp Tyr Trp Arg His Leu Val Val Gly Ile Ala Ala Leu Ser
```

```
              115                 120                 125
Asn Ala Asn Lys Pro Ser Ala Ser Pro Val Lys Val Leu Ser Asp Lys
            130                 135                 140

Ile Thr Gln Ile Tyr Ser Asp Ile Lys Leu Pro Asn Ser Ala Ser Val
145                 150                 155                 160

Glu Gln Ile Gln Ser Lys Met Gln Glu Leu Ser Asp Leu Leu Glu Glu
                165                 170                 175

Leu Arg Asp Ser Phe Asp Gly Tyr Ile Ser Asn Ala Phe Ala Gly Gln
            180                 185                 190

Ile Gln Leu Asn Phe Gln Ala Thr Ala Gln Glu Ala Val Ala Ala Ala
        195                 200                 205

Ala Val Arg Leu Leu Asn Gly Asn Asp Gln Ile Ala Gln Leu Tyr Lys
        210                 215                 220

Asp Leu Val Lys Leu Gln Arg His Ala Gly Ile Arg Lys Ala Met Glu
225                 230                 235                 240

Lys Leu Ala Ala Gln Glu Thr Glu Phe Asp Leu Ser Met Ile Val Gly
                245                 250                 255

Gln Val Lys Leu Tyr Ala Asp Leu Met Thr Thr Glu Ser Phe Ser
            260                 265                 270

<210> SEQ ID NO 21
<211> LENGTH: 272
<212> TYPE: PRT
<213> ORGANISM: Artificial Sequence
<220> FEATURE:
<223> OTHER INFORMATION: Kato

<400> SEQUENCE: 21

Ser Ala Ser Ala Ile Glu Leu Gly Asp Glu Gly Gly Leu Glu Cys Gly
1               5                   10                  15

Pro Tyr Ala Lys Val Gly Val Gly Gly Met Ile Thr Gly Val Glu
                20                  25                  30

Ser Thr Arg Leu Asp Pro Ala Asp Val Asp Gly Lys Lys His Leu Ser
            35                  40                  45

Leu Thr Thr Gly Leu Pro Phe Gly Gly Thr Leu Ala Ala Gly Met Thr
        50                  55                  60

Ile Ala Pro Gly Phe Arg Ala Glu Leu Gly Val Met Tyr Leu Thr Asn
65                  70                  75                  80

Val Lys Leu Thr Pro Pro Gln Pro Thr Ile Met Pro Ile Ser Ile Ala
                85                  90                  95

Asp Arg Asp Phe Gly Val Asp Arg Ile Ala Trp Leu Lys Glu Tyr Ala
            100                 105                 110

Gly Ile Asp Tyr Trp Arg His Leu Val Val Gly Val Thr Ala Met Ser
        115                 120                 125

Asn Ala Asn Lys Pro Ser Val Ser Pro Val Lys Val Leu Ser Asp Lys
        130                 135                 140

Ile Val Gln Ile Tyr Arg Asp Ile Lys Leu Pro Asn Ser Ala Ser Val
145                 150                 155                 160

Glu Gln Ile Gln Asn Lys Met Gln Glu Leu Asn Asp Ile Leu Glu Glu
                165                 170                 175

Ile Arg Asp Ser Phe Asp Gly Cys Ile Gly Gly Asn Ala Phe Ala Asn
            180                 185                 190

Gln Ile Gln Leu Asn Phe Gln Ala Thr Ala Gln Glu Ala Ala Ala Ala
        195                 200                 205

Ala Ala Val Arg Val Leu Asn Asn Asn Asp Gln Ile Ile Gln Leu Tyr
```

```
            210                 215                 220

Lys Asp Leu Val Lys Leu Lys Arg His Ala Gly Ile Lys Lys Ala Met
225                 230                 235                 240

Glu Lys Leu Ala Ala Gln Thr Glu Phe Asp Leu Ser Met Ile Val
                245                 250                 255

Gly Gln Val Lys Leu Tyr Ala Asp Leu Phe Thr Thr Glu Ser Phe Ser
                260                 265                 270

<210> SEQ ID NO 22
<211> LENGTH: 272
<212> TYPE: PRT
<213> ORGANISM: Artificial Sequence
<220> FEATURE:
<223> OTHER INFORMATION: Shimokoshi

<400> SEQUENCE: 22

Ser Ala Asn Ala Ile Glu Leu Asp Glu Asn Ser Leu Glu Cys Gly Pro
1               5                   10                  15

Tyr Ala Lys Val Gly Ile Val Gly Gly Val Leu Ser Gly Val Glu Ser
                20                  25                  30

Ala Arg Leu Asp Pro Ala Asp Ser Glu Gly Lys Lys His Leu Pro Leu
                35                  40                  45

Ile Lys Gly Met Pro Phe Gly Val Thr Leu Ala Ala Gly Met Thr Ile
            50                  55                  60

Thr Pro Gly Val Arg Ala Glu Ile Ser Ala Met Tyr Leu Met Asn Val
65                  70                  75                  80

Lys Leu Thr Pro Pro Gln Pro Asn Ile Met Pro Ile Ser Ile Ala Asp
                85                  90                  95

Arg Asp Ile Gly Val Asp Arg Ile Ala Trp Leu Lys Asn Tyr Ala Gly
            100                 105                 110

Ile Asp Tyr Trp Arg Asp Val Val Gly Ile Thr Ala Leu Ser Asn
            115                 120                 125

Ala Asn Lys Pro Asn Val Ser Ala Val Lys Val Leu Ser Asp Lys Ile
        130                 135                 140

Ser Gln Ile Tyr Ala Asp Ile Lys Leu Pro Asp Ser Ala Ser Val Glu
145                 150                 155                 160

Gln Ile Gln Asn Lys Val Gln Glu Leu Asn Lys Val Leu Glu Asp Val
                165                 170                 175

Arg Glu Ser Phe Asp Gly Phe Ile Leu Asn Ala Phe Ala Gln Gln Val
            180                 185                 190

Gln Leu Asn Phe Ala Ala Thr Ala Gln Glu Ala Ala Ala Ala Ala
            195                 200                 205

Val Arg Ala Leu Asn Asp Gly Glu Asn Asn Gly Ile Ile Gln Leu Tyr
        210                 215                 220

Lys Asp Leu Tyr Lys Leu Gln Arg His Val Ala Leu Lys Lys Ser Met
225                 230                 235                 240

Glu Gln Leu Gly Ala Glu Glu Ile Glu Phe Asp Leu His Met Ala Val
                245                 250                 255

Gly Gln Val Lys Leu Tyr Ala Asp Leu Phe Thr Ile Asp Ser Phe Ser
                260                 265                 270

<210> SEQ ID NO 23
<211> LENGTH: 271
<212> TYPE: PRT
<213> ORGANISM: Artificial Sequence
<220> FEATURE:
<223> OTHER INFORMATION: Universal conserved blocks
```

-continued

```
<400> SEQUENCE: 23

Ser Ala Ser Ala Ile Glu Leu Gly Asp Glu Gly Leu Glu Cys Gly
1               5                   10                  15

Pro Tyr Ala Lys Val Gly Val Gly Gly Met Ile Thr Gly Val Glu
            20                  25                  30

Ser Thr Arg Leu Asp Ser Ala Asp Ala Asp Gly Lys Lys His Leu Pro
        35                  40                  45

Leu Thr Thr Gly Met Pro Phe Gly Gly Thr Leu Ala Ala Gly Met Thr
    50                  55                  60

Ile Ala Pro Gly Phe Arg Ala Glu Leu Gly Val Met Tyr Leu Thr Asn
65                  70                  75                  80

Ile Lys Leu Thr Pro Pro Gln Pro Thr Ile Met Pro Ile Ser Ile Ala
                85                  90                  95

Asp Arg Asp Phe Gly Val Asp Arg Ile Ala Trp Leu Lys Asn Tyr Ala
            100                 105                 110

Gly Ile Asp Tyr Trp Arg His Leu Val Val Gly Val Thr Ala Leu Ser
        115                 120                 125

Asn Ala Asn Lys Pro Ser Val Ser Pro Val Lys Val Leu Ser Asp Lys
    130                 135                 140

Ile Thr Gln Ile Tyr Ser Asp Ile Lys Leu Pro Asn Ser Ala Ser Val
145                 150                 155                 160

Glu Gln Ile Gln Asn Lys Met Gln Glu Leu Asn Asp Val Leu Glu Glu
                165                 170                 175

Leu Arg Asp Ser Phe Asp Gly Tyr Ile Gly Asn Ala Phe Ala Asn Gln
            180                 185                 190

Ile Gln Leu Asn Phe Gln Ala Thr Ala Gln Glu Ala Ala Ala Ala
        195                 200                 205

Ala Val Arg Ala Leu Asn Gly Asn Asp Gln Ile Ile Gln Leu Tyr Lys
    210                 215                 220

Asp Leu Val Lys Leu Gln Arg His Ala Gly Ile Lys Lys Ala Met Glu
225                 230                 235                 240

Lys Leu Ala Ala Gln Glu Thr Glu Phe Asp Leu Ser Met Ile Val Gly
                245                 250                 255

Gln Val Lys Leu Tyr Ala Asp Leu Phe Thr Thr Glu Ser Phe Ser
            260                 265                 270

<210> SEQ ID NO 24
<211> LENGTH: 251
<212> TYPE: PRT
<213> ORGANISM: Artificial Sequence
<220> FEATURE:
<223> OTHER INFORMATION: cTSA56_Boryong

<400> SEQUENCE: 24

Ser Ala Ser Ala Ile Glu Leu Glu Asp Glu Val Gly Leu Glu Cys Gly
1               5                   10                  15

Pro Tyr Ala Lys Val Gly Val Gly Gly Met Ile Thr Gly Ala Glu
            20                  25                  30

Ser Thr Arg Leu Asp Ser Thr Asp Ser Glu Gly Lys Lys His Pro Gly
        35                  40                  45

Phe Arg Ala Glu Leu Gly Val Met Tyr Leu Arg Asn Ile Lys Leu Thr
    50                  55                  60

Pro Pro Gln Pro Thr Met Met Pro Ile Ser Ile Ala Asp Arg Asp Phe
65                  70                  75                  80
```

```
Gly Ile Asp Arg Ile Ala Trp Leu Lys Asn Cys Ala Gly Ile Asp Tyr
                85                  90                  95

Trp Arg Ser Leu Val Val Gly Leu Ala Ala Leu Ser Asn Ala Asn Lys
            100                 105                 110

Pro Ser Ala Ser Pro Val Lys Val Leu Ser Asp Lys Ile Ile Gln Ile
            115                 120                 125

Tyr Ser Asp Ile Lys Leu Pro Asn Ser Ala Ser Ile Glu Gln Ile Gln
            130                 135                 140

Ser Lys Ile Gln Glu Leu Gly Asp Thr Leu Glu Leu Arg Asp Ser
145                 150                 155                 160

Phe Asp Gly Tyr Ile Asn Asn Ala Phe Val Asn Gln Ile His Leu Asn
                165                 170                 175

Phe Gln Ala Thr Ala Gln Glu Ala Val Ala Ala Ala Val Arg Leu
                180                 185                 190

Leu Asn Gly Ser Asp Gln Ile Ala Gln Leu Tyr Lys Asp Leu Val Lys
            195                 200                 205

Leu Gln Arg His Ala Gly Ile Arg Lys Ala Met Glu Lys Leu Ala Ala
            210                 215                 220

Gln Glu Thr Glu Phe Asp Leu Ser Met Val Val Gly Gln Val Lys Leu
225                 230                 235                 240

Tyr Ala Asp Leu Val Thr Thr Glu Ser Phe Ser
                245                 250

<210> SEQ ID NO 25
<211> LENGTH: 20
<212> TYPE: PRT
<213> ORGANISM: Artificial Sequence
<220> FEATURE:
<223> OTHER INFORMATION: Sequence removed from Boryong genotype
      conserved block 1

<400> SEQUENCE: 25

Leu Ser Leu Thr Thr Gly Leu Pro Phe Gly Gly Thr Leu Ala Ala Gly
1               5                   10                  15

Met Thr Ile Ala
            20
```